US011414681B2

(12) United States Patent
Ghadessy et al.

(10) Patent No.: US 11,414,681 B2
(45) Date of Patent: *Aug. 16, 2022

(54) MUTANTS OF THE BACTERIOPHAGE LAMBDA INTEGRASE

(71) Applicant: AGENCY FOR SCIENCE, TECHNOLOGY AND RESEARCH, Singapore (SG)

(72) Inventors: Farid Ghadessy, Biopolis (SG); Jia Wei Siau, Singapore (SG); Peter Droge, Singapore (SG); Harshyaa Makhija, Singapore (SG); Shree Harsh Vijaya Chandra, Singapore (SG); Sabrina Peter, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/430,410

(22) Filed: Jun. 3, 2019

(65) Prior Publication Data

US 2020/0063165 A1 Feb. 27, 2020

Related U.S. Application Data

(63) Continuation of application No. 15/502,783, filed as application No. PCT/SG2015/050255 on Aug. 11, 2015, now Pat. No. 10,344,301.

(30) Foreign Application Priority Data

Aug. 8, 2014 (GB) ..................... 1414130

(51) Int. Cl.
| | |
|---|---|
| *C12N 9/12* | (2006.01) |
| *C12N 9/22* | (2006.01) |
| *C12N 1/15* | (2006.01) |
| *C12N 1/21* | (2006.01) |
| *C12P 19/34* | (2006.01) |
| *C12N 15/90* | (2006.01) |

(52) U.S. Cl.
CPC ......... *C12N 15/907* (2013.01); *C12N 9/1241* (2013.01); *C12N 9/22* (2013.01); *C12N 15/90* (2013.01); *C12N 2795/10322* (2013.01)

(58) Field of Classification Search
None
See application file for complete search history.

(56) References Cited

U.S. PATENT DOCUMENTS

| | | | | |
|---|---|---|---|---|
| 10,344,301 | B2 * | 7/2019 | Ghadessy | C12N 15/907 |
| 2010/0192985 | A1 * | 8/2010 | Aehle | C11D 3/38645 |
| | | | | 134/26 |
| 2013/0017578 | A1 | 1/2013 | Ghadessy et al. | |

FOREIGN PATENT DOCUMENTS

CA 2522166 12/2002

OTHER PUBLICATIONS

Zhang et al., Structure 26:1474-1485, 2018 (Year: 2018).*
Spengler et al., Cell 42:325-334, 1985 (Year: 1985).*
Fogg et al., J. Mol. Biol. 426:2703-2716, Jul. 2014 (Year: 2014).*
Dorgai, et al., "Identifying Determinants of Recombination Specificity: Construction and Characterization of Mutant Bacteriophage Integrases," J. Mol Biol., 1995, pp. 178-188, vol. 252.
Extended European Search Report for European Application No. 15829802.6, dated Nov. 28, 2017.
Siau, et al., "Directed evolution of a integrase activity and specificity by genetic depression," Protein Engineering, Design and Selection, Mar. 18, 2015, pp. 211-220, vol. 28, No. 7.
Tay, et al., "Selection of bacteriophage λ integrases with altered recombination specificity by in vitro compartmentalization," Nucleic Acids Research, Dec. 4, 2009, E25, vol. 38, No. 7.
The International Search Report of PCT Application No. PCT/SG2015/050255, dated Nov. 6, 2015, 5 pgs.
The Notification of Transmittal of the International Search Report and the Written Opinion of the International Searching Authority of PCT Application No. PCT/SG2015/050255, dated Aug. 11, 2015, 1 pg.
The Written Opinion of the International Searching Authority, dated Nov. 6, 2015, 6 pgs.
The International Preliminary Report on Patentability of PCT Application No. PCT/SG2015/050255, dated Feb. 14, 2017, 7 pgs.
UniProt Database Accession No. V0VKX3, <https://www.uniprot.org/uniprot/V0VKX3.txt?version=1> Jan. 2014, 1 pg.

* cited by examiner

*Primary Examiner* — David Steadman
(74) *Attorney, Agent, or Firm* — Womble Bond Dickinson (US) LLP

(57) ABSTRACT

The present invention refers to lambda integrases comprising at least one amino acid mutation at positions 43, 319 and 336 of the lambda integrase as set forth in SEQ ID NO: 1. The invention further refers to nucleic acid molecules comprising the nucleotide sequence encoding the mutant lambda integrase and to host cells containing these nucleic acid molecules. The invention also refers to methods of recombining a nucleic acid of interest into a target nucleic acid in the presence of the mutant lambda integrase and sequence specific recombination kits.

13 Claims, 10 Drawing Sheets

Specification includes a Sequence Listing.

FIG 1

| | Core-binding sequence | | | | | | | Overlap sequence | | | | | | Core-binding sequence | | | | | | |
|---|---|---|---|---|---|---|---|---|---|---|---|---|---|---|---|---|---|---|---|---|
| attB | C | T | G | C | T | T | T | T | T | T | A | T | A | C | T | A | A | C | T | T | G |(SEQ ID No.:5)
| attH | C | T | G | C | T | T | T | C | T | T | A | T | A | C | C | A | A | G | T | G | G |(SEQ ID No.:7)
| attH4X | A | C | G | C | T | T | T | A | T | T | T | C | A | T | T | A | A | G | T | T | G |(SEQ ID No.:31)
| attP | C | A | G | C | T | T | T | T | T | T | A | T | A | C | T | A | A | G | T | T | G |(SEQ ID No.:6)
| attPH | C | A | G | C | T | T | T | C | T | T | A | T | A | C | C | A | A | G | T | G | G |(SEQ ID No.:8)
| attP4X | C | A | G | C | T | T | T | A | T | T | T | C | A | T | T | A | A | G | T | T | G |(SEQ ID No.:9)

FIGS 3A-B
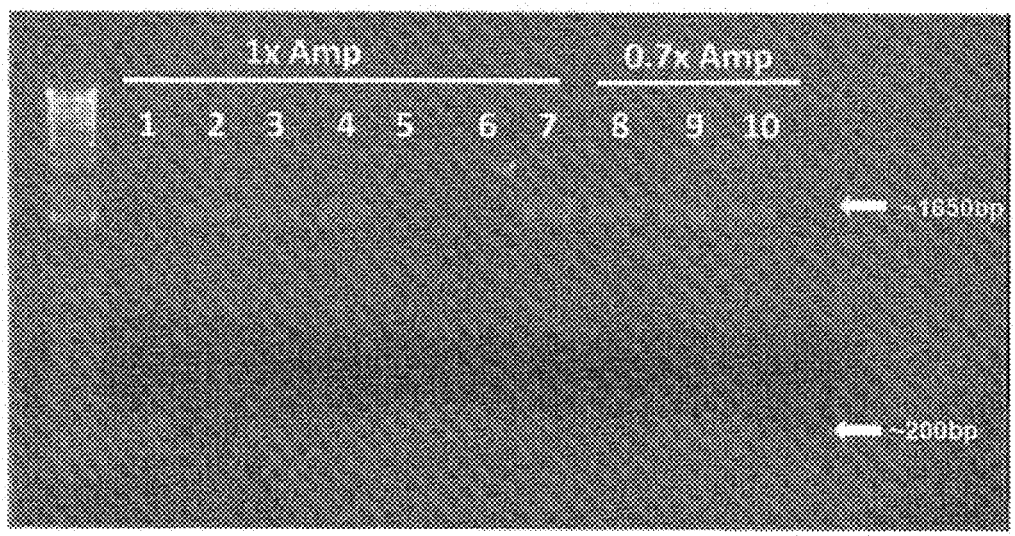
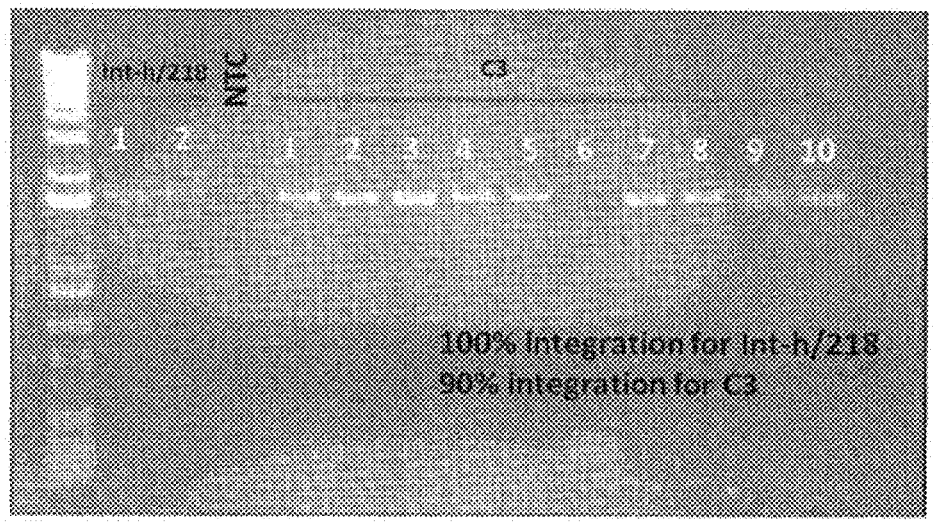

FIG 3C tgaatccgttgaagcCTGCTTTTTTTATACTAAGTTGGCATTATAAAAAAGCATTGCTTA
TCAATTTGTTGCAACGAACAGGTCACTATCAGTCAAAATAAAATCATTATTTGA
TTTCCCGGTGATGTTCAGGTGGCACTTTTCGGGGAAATGTGCGCGGAACCCCT
ATTTGTTTATTTTTCTAAATACATTCAAATATGTATCCGCTCATGAGACAATAACC
CTGATAAATGCTTCAATAATATTGAAAAAGGAAGAGTATGAGTATTCAACATTTC
CGTGTCGCCCTTATTCCCTTTTTTGCGGCATTTTGCCTTCCTGTTTTTGCTCACC
CAGAAACGCTGGTGAAAGTAAAAGATGCTGAAGATCAGTTGGGTGCACGAGT
GGGTTACATCGAACTGGATCTCAACAGCGGTAAGATCCTTGAGAGTTTTCGCC
CCGAAGAACGTTTTCCAATGATGAGCACTTTTAAAGTTCTGCTATGTGGCGCG
GTATTATCCCGTATTGACGCCGGGCAAGAGCAACTCGGTCGCCGCATACACT
ATTCTCAGAATGACTTGGTTGAGTACTCACCAGTCACAGAAAGCATCTTACG
GATGGCATGACAGTAAGAGAATTATGCAGTGCTGCCATAACCATGAGTGATA
ACACTGCGGCCAACTTACTTCTGACAACGATCGGAGGACCGAAGGAGCTAAC
CGCTTTTTTGCACAACATGGGGGATCATGTAACTCGCCTTGATCGTTGGGAAC
CGGAGCTGAATGAAGCCATACCAAACGACGAGCGTGACACCACGATGCCTG
CAGCAATGGCAACAACGTTGCGCAAACTATTAACTGGCGAACTACTTACTCTA
GCTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTGGA
GCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGA
TGAACGAAATAGACAGATCGCTGAGATAGGTGCCTCACTGATTAAGCATTGGT
AACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCC
CTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTT
CCGAAGGTAACTGGCTTCAGCAGAGCGCAGATACCAAATACTGTCCTTCTAGTG
TAGGAATTCCACAGAATTCCGTCTGTTACAGGTCACTAATACCATCTAAGTAGT
TGATTCATAGTGACTGCATATATTGTGTTTACAGTATTATGTAGTCTGTTTTTT
ATGCAAAATCTAATTTAATATATTGATATTTATATCATTTTACGTTTCTCGTTCA
GCTTTTTTATACTAACTTGagcgaaacgggaaggtaaaagacat (SEQ ID No. :32)

FIGS 5A-B
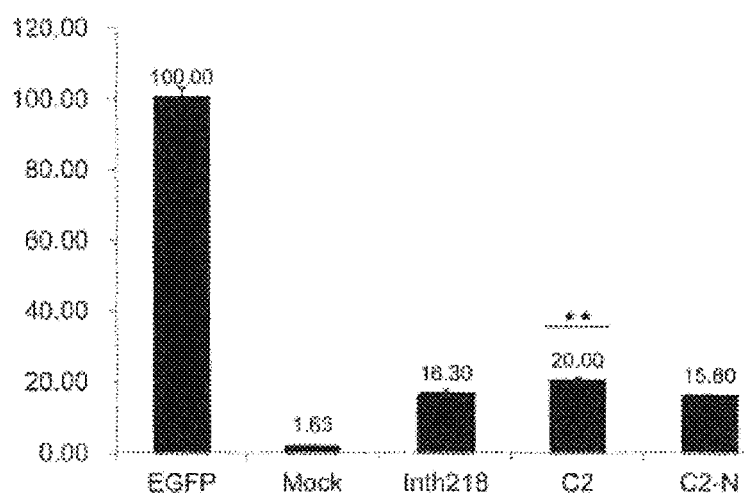
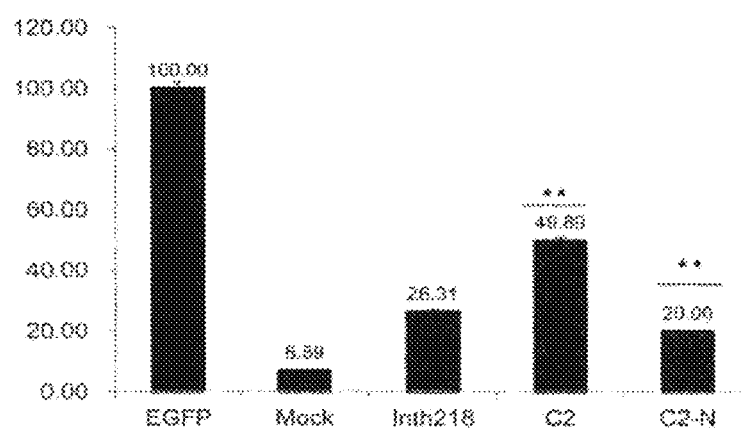

FIGS 5C-D
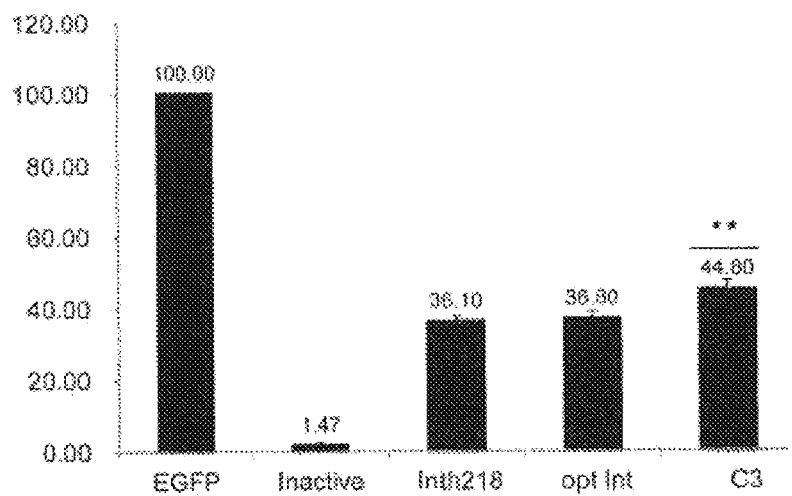
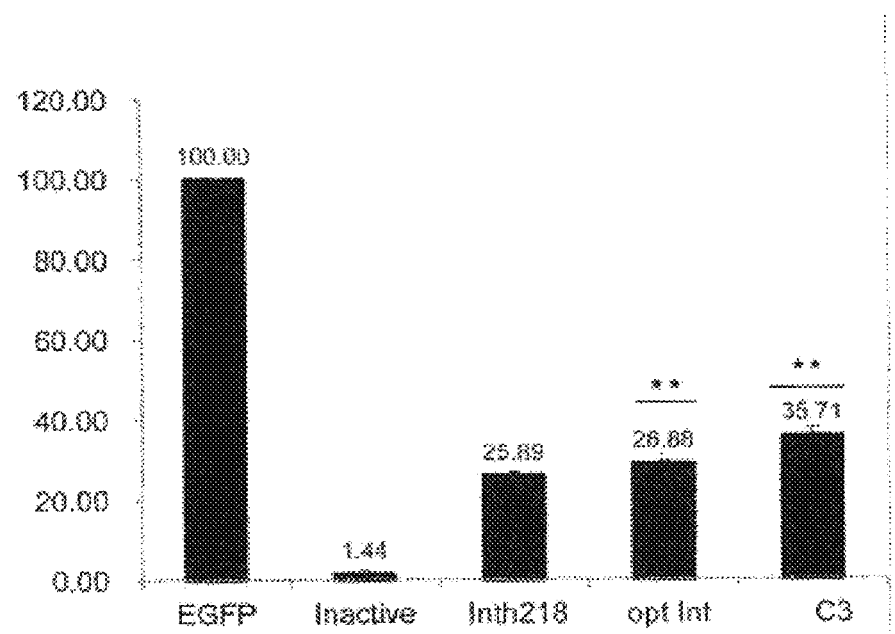

FIG 6B clone 3
ctttatgacccagtcatcgttggtttggtcttttcacatagtcccatgtttcttggagattt
tgttcattccttctcattcttttttctctaatcttgtcctc*ATGCTTTATTTCATTAAGTTG*
*GCATTATAAAAAGCATTGCTTATCAATTTGTTGCAACGAACAGGTCACTATCAGTCAAAAT*
*ACAATCATTATTTGATTTCAATTTTGTCCCACTCCCTCCCG*AATTCTACCGGGTAGGGGAGG
CGCTTTTCCCAAGGCAGTCTGGAGCATGCGCTTTAGCAGCCCCGCTGGGCACTTGGCGCTAC
ACAAGTGGCCTCTGGCCTCGCACACATTCCACATCCACCGGTAGGCGCCAACCGGCTCCGTT
CTTTGGTGGCCCCTTCGCGCCACCTTCTACTCCTCCCCTAGTCAGGAAGTTCCCCCCCGCCC
CGCAGCTCGCGTCGTGCAGGACGTGACAAATGGAAGTAGCACGTCTCACTAGTCTCGTGCAG
ATGGACAGCACCGCTGAGCAATGGAAGCGGGTAGGCCTTTGGGGCAGCGGCCAATAGCAGCT
Targeted locus: Chromosome 19 (35188923-35188943) (SEQ ID No. :33)

clone 19
gattcggtaaccaatcaaatgtaagcttggtcttttcacataatcccatatttttggaggc
tttgttcatttcttttcattcttttttctctaatctgtcttc*ATGCTTTATTTCATTAAGTT*
*GGCATTATAAAAAGCATTGCTTATCAATTTGTTGCAACGAACAGGTCACTATCAGTCAAAA*
*TACAATCATTATTTGATTTCAATTTTGTCCCACTCCCTCCCG*AATTCTACCGGGTAGGGGAG
GCGCTTTTCCCAAGGCAGTCTGGAGCATGCGCTTTAGCAGCCCCGCTGGGCACTTGGCGCTA
CACAAGTGGCCTCTGGCCTCGCACACATTCCACATCCACCGGTAGGCGCCAACCGGCTCCGT
TCTTTGGTGGCCCCTTCGCGCCACCTTCTACTCCTCCCCTAGTCAGGAAGTTCCCCCCCGCC
CCGCAGCTCGCGTCGTGCAGGACGTGACAAATGGAAGTAGCACGTCTCACTAGTCTCGTGCA
GATGGACAGCACCGCTGAGCAATGGAAGCGGGTAGGCCTTTGGGGCAGCGGCCAATAGCAGC
Targeted locus: Chromosome 2 (153753805-153753825) (SEQ ID No. :34)

MUTANTS OF THE BACTERIOPHAGE LAMBDA INTEGRASE

CROSS-REFERENCE TO RELATED APPLICATIONS

This patent application is a continuation of U.S. patent application Ser. No. 15/502,783, filed Feb. 8, 2017, entitled MUTANTS OF THE BACTERIOPHAGE LAMBDA INTEGRASE, which is a U.S. National Phase Application under 35 U.S.C. § 371 of International Application No. PCT/SG2015/050255, filed Aug. 11, 2015, and which claims priority to Great Britain Patent Application No. 1414130.3, filed Aug. 8, 2014.

INCORPORATION BY REFERENCE

This patent application incorporates by reference the material (i.e., Sequence Listing) in the ASCII text file named 9322P054C_Amended_SequenceListing_Updated, created on Dec. 13, 2021, having a file size of 39.7 kilobytes.

TECHNICAL FIELD

The present invention relates to mutants of bacteriophage lambda integrases and to nucleic acid molecules comprising a nucleotide sequence encoding such mutants.

BACKGROUND

Phage integrases are enzymes that mediate unidirectional site-specific recombination between two DNA recognition sequences, the phage attachment site, attP, and the bacterial attachment site, attB. Integrases may be grouped into two major families, the tyrosine recombinases and the serine recombinases, based on their mode of catalysis.

Tyrosine family integrases, such as lambda integrase, utilize a catalytic tyrosine to mediate strand cleavage, tend to recognize longer attP sequences, and require other proteins encoded by the phage or the host bacteria.

Phage integrases from the serine family are larger, use a catalytic serine for strand cleavage, recognize shorter attP sequences, and do not require host cofactors. Phage integrases mediate efficient site-specific recombination between two different sequences that are relatively short, yet long enough to be specific on a genomic scale.

These properties give phage integrases growing importance for the genetic manipulation of living eukaryotic cells, especially those with large genomes such as mammals and most plants, for which there are few tools for precise manipulation of the genome.

The use of lambda integrases has been subject to extensive research for catalyzing site-specific DNA recombination. For example, two mutant lambda integrases, Int-h (E174K) and its derivative Int-h/218 (E174K/E718K) have been described and were shown to catalyze intermolecular recombination reactions at least as efficiently as the corresponding intramolecular recombination reactions in human cells. Although the presence of arm-site sequences have been shown to increase the recombination of core-sites by Int-h/218 in vivo, given the absence of an attB site in the human genome, recombination reactions occur in non-cognate sites in an essentially random manner.

This makes it difficult to engineer cell lines in a controlled, reproducible fashion.

Therefore, there remains a need to provide mutant integrases having greater efficiency and specificity in catalyzing site specific recombination reactions.

SUMMARY

In one aspect, there is provided a lambda integrase comprising at least one amino acid mutation selected from the group consisting of I43F, E319G and D336V.

In another aspect, there is provided a lambda integrase comprising an amino acid mutation at at least one of positions 336, 319 and 43 of the lambda integrase as set forth in SEQ ID NO: 1.

In another aspect, there is provided a nucleic acid molecule. The nucleic acid molecule includes a nucleotide sequence encoding a mutant as described herein.

In a further aspect, there is provided a host cell. The host cell includes a nucleic acid molecule as described herein.

In yet another aspect, there is provided a method of recombining a nucleic acid of interest into a target nucleic acid. The method includes contacting a targeting nucleic acid comprising the nucleic acid of interest with the target nucleic acid in the presence of a mutant as described herein.

In yet a further aspect, there is provided a sequence specific recombination kit. The kit includes a targeting nucleic acid into which a nucleic acid of interest can be inserted, and a mutant as described herein.

Definitions

The following words and terms used herein shall have the meaning indicated:

The term "mutant" refers to a protein arising as a result of a mutation or a recombinant DNA procedure.

The term "Int" or "integrase" refers to the lambda phage integrase protein.

As used herein, "nucleic acid" refers to any nucleic acid in any possible configuration, such as linearized single stranded, double stranded or a combination thereof. Nucleic acids may include, but are not limited to DNA molecules (e.g., cDNA or genomic DNA), RNA molecules (e.g., mRNA), analogues of the DNA or RNA generated using nucleotide analogues or using nucleic acid chemistry, cDNA synthetic DNA, a copolymer of DNA and RNA, oligonucleotides, and PNA (protein nucleic acids). DNA or RNA may be of genomic or synthetic origin and may be single or double stranded. A respective nucleic acid may furthermore contain non-natural nucleotide analogues and/or be linked to an affinity tag or a label.

As used herein, nucleotides include nucleoside mono-, di-, and triphosphates. Nucleotides also include modified-nucleotides, such as, but not limited to, phophorothioate nucleotides and deazapurine nucleotides and other nucleotide analogs.

An "attB/attP reaction" or a "B/P reaction" is a recombination reaction between an attB recognition site and an attP recognition site mediated by an Int.

An "attH/attPH reaction" or an "B/P reaction" is a recombination reaction between an attB recognition site and an attPH recognition site mediated by an Int.

An "att site" is an attachment site on a DNA molecule for an integrase or integrase complex. As used herein, "act site" is generally used interchangeably with "recognition site," described in greater detail below. Generally, "att site" is used to refer to a particular type of recognition site, such as, for example, an attB, an attP, an attL, or an attR site.

"Chromosomally-integrated" or "integrated" refers to the integration of a foreign gene or nucleotide sequence into a host genome by covalent bonds that are formed with the host DNA.

"Deletion reaction" and "excision reaction" are used interchangeably and refer to a recombination reaction between two recognition sites that are on the same DNA molecule and are in direct orientation with respect to one another. This reaction results in the removal of a nucleotide sequence that is positioned between the two recognition sites.

"Direct orientation" refers to an orientation of two or more recognition sites such that 15 base pair core regions of the recognition sites are oriented in the same 5' to 3' direction. "Direct repeat," as used herein, refers to two or more recognition sites that are in direct orientation with respect to each other.

"Donor," "donor molecule," "donor sequence," and "donor DNA" are used interchangeably to refer to a nucleotide sequence that has been selected to undergo recombination with the target DNA sequence using site-directed recombination. The donor nucleotide sequence can be any nucleotide sequence, such as, for example, a gene, an expression cassette, a promoter, a molecular marker, a selectable marker, a visible marker, a portion of any of these, or the like. The donor DNA sequence comprises at least one recombinase recognition site.

"Endogenous" as used herein means "of the same origin," i.e., derived from a host cell.

"Expression cassette" as used herein includes a nucleotide sequence that is capable of directing or driving the expression of another nucleotide sequence in an appropriate host cell. An expression cassette typically comprises a promoter operably linked to a nucleotide sequence, such as a nucleotide sequence of interest, for example, which is operably linked to a termination signal. The expression cassette also typically comprises sequences needed for proper translation of the nucleotide sequence. The nucleotide sequence of interest usually codes for a protein of interest but can also code for a functional RNA of interest, for example antisense RNA or a non-translated RNA that, in the sense or antisense direction, inhibits expression of a particular gene, e.g., antisense RNA. The expression cassette comprising the nucleotide sequence can be chimeric, meaning that at least one of its components is heterologous with respect to at least one of its other components. The expression cassette can include endogenous DNA that has been obtained in a recombinant form and is useful for heterologous expression. Typically, however, the expression cassette is heterologous with respect to the host; that is, the particular DNA sequence of the expression cassette does not occur naturally in the host cell and must be introduced into the host cell or an ancestor of the host cell through a transformation event. The expression of the nucleotide sequence in the expression cassette can be under the control of any suitable promoter, such as for example, either a constitutive promoter or an inducible promoter that initiates transcription only when the host cell is exposed to some particular external stimulus. In the case of a multicellular organism, the promoter can also be specific to a particular tissue or organ or stage of development.

A "foreign" gene or DNA refers to a gene or a nucleotide sequence that is not normally found in the host organism but can be introduced by gene transfer. Foreign genes and DNA that are not integrated into the genome of the host cell are referred to as "extrachromosomal."

The term "gene" is used broadly to include any segment of a nucleotide sequence associated with a biological function. Thus, a gene can include a coding sequence either with or without the regulatory sequences required for its expression. Further, a gene can include both exon and intron sequences or can include only exon sequences. A gene can also include non-expressed DNA segments that, for example, form recognition sequences for other proteins. A "portion of a gene" or "an incomplete gene" as used herein means a part of a gene that is non-functional because it does not contain all of the sequence needed for functionality. The portion can be the 5' portion of a gene (i.e., the sequence at the 3' end of the gene is not present), or the portion can be the 3' portion of a gene (i.e., the sequence at the 5' end of the gene is not present). The 5' and 3' portions can be nonfunctional on their own, but when the 5' and 3' portions are operably linked, the gene is "functional" or "complete."

"Gene of interest," "sequence of interest," "nucleic acid of interest," and "DNA of interest" are used interchangeably and include any nucleotide sequence which, when transferred to a cell, confers upon the cell a desired characteristic, such as virus resistance, insect resistance, antibiotic stress resistance, disease resistance, resistance to other pests, herbicide tolerance, improved nutritional value, improved performance in an industrial process, or altered reproductive capability, for example. The sequence of interest can also be one that is transferred to cell lines or mammals or plants for the production of commercially valuable enzymes or metabolites. In this context, the "target nucleic acid" as used herein refers to a nucleotide sequence containing at least one recognition site. The target nucleotide sequence can be a gene, an expression cassette, a promoter, a molecular marker, a portion of any of the above, or the like. The target nucleic acid can be stably transformed into a host cell to create a transformed cell line comprising the target sequence integrated into a chromosomal location in the genome. Accordingly, in some embodiments, the target nucleic acid can include genomic DNA. The genomic DNA can be comprised in a cell. In other embodiments, the target nucleic acid can include a sequence selected from the group consisting of an attH sequence (SEQ ID NO: 7) and an attH4X sequence (SEQ ID NO: 31).

"Genome" refers to the complete genetic material of an organism.

"Heterologous" as used herein means "of different natural origin," i.e., representing a non-natural state. For example, if a host cell is transformed with a gene derived from another organism, particularly from another species, that gene is heterologous with respect to both the host cell and descendants of the host cell that carry the gene. Similarly, "heterologous" refers to a nucleotide sequence which is derived from a natural or original cell type and is inserted into that same natural or original cell type, but which is present in a non-natural state, such as, for example, in a different copy number, under the control of different regulatory elements, or the like.

To "identify" a recombination product means that the recombination product is detected and distinguished from both the target and donor sequences. There are many means for identifying a recombination product. For example, a selectable marker gene can be used, whereby site-specific integration results in the selectable marker becoming operatively linked with a promoter only in a recombinant product. Alternatively, a visible marker gene can be used, whereby a gain or loss of marker gene expression identifies a recombination product. Alternatively, a negative selectable marker gene car be used, whereby a loss or lack of expression of the marker gene identifies a recombination product. Additionally, molecular markers that are characteristic of the target sequence and/or donor sequence can be used, such that the molecular marker pattern is unique for the recombination product.

"Integrase" as used herein refers to a bacteriophage lambda-derived integrase, including wild-type integrase and any of a variety of mutant or modified integrases. "Integrase complex" as used herein refers to a complex comprising integrase and integration host factor (IHF). "Integrase complex" as used herein may also refer to a complex comprising integrase, integration host factor, and a bacteriophage lambda-derived excisionase (Xis). Further, as used herein, "Int" refers to both "integrase" and "integrase complex."

An "integrase-mediated recombination product" is a recombination product formed between target and donor sequences in the presence of an integrase or integrase complex. The integrase-mediated recombination results in strand exchange between at least one recombinase recognition site on the target and at least one recombinase recognition site on the donor, whereby a recombination product is formed. Consistent with the usage defined above, "Int-mediated recombination" or "Int-mediated recombination product" means a recombination or recombination product that is mediated by either an integrase or an integrase complex.

"Intramolecular recombination" refers to recombination between recognition sites on a single nucleic acid molecule. Recombination between recognition sites on different molecules is termed "intermolecular recombination."

"Intrachromosomal recombination" refers to recombination between recognition sites on a single chromosome. Recombination between recognition sites on different chromosomes is termed "interchromosomal recombination."

An "inversion reaction" refers to an intramolecular recombination reaction between two att sites that are in inverted orientation with respect to each other. For example, an inversion reaction can be effected by an intramolecular reaction between either an attB site and an attP site in inverted orientation or an attL site and an attR site in inverted orientation.

"Inverted orientation" refers to an orientation of two recognition sites such that 15 base pair core regions of the recognition sites are oriented in the opposite 5' to 3' direction.

"Operably linked" or "operatively linked" refers to the relationship between two or more nucleotide sequences that interact physically or functionally. For example, a promoter or regulatory nucleotide sequence is said to be operably linked to a nucleotide sequence that codes for an RNA or a protein if the two sequences are situated such that the regulatory nucleotide sequence will affect the expression level of the coding or structural nucleotide sequence. A 5' portion of a gene is operatively or operably linked with a 3' portion of a gene if the two portions are situated to form a functional gene.

"Recognition site" or "recombination site" refers to a nucleotide sequence that can be recognized by a recombinase protein. The recognition site is the nucleotide sequence at which binding, cleavage, and strand exchange is performed by the recombinase and any associated accessory proteins. Integrase or integrase complex recognizes recognition sites comprising an attB, attL, attR, attP, and/or suitable mutations of such sites. The attB site can be approximately 25-30 bps and includes two 7 bp core sequences and a 7 bp overlap (or spacer) region, whereas the attP site can be approximately 240 bps and comprises binding sites for an integrase and one or more accessory proteins. The attB and attP sites can be recombined together by Int or, alternatively, the attL and attR sites can be recombined together by Int.

"Recombinase" refers to an enzyme that is capable of performing site-specific recombination of DNA. Recombinase enzymes possess endonuclease and ligase activities. A recombinase can function either as a single protein or as a part of a complex of proteins. As used herein integrase and integrase complex are recombinases.

Generally, if a recombinase-mediated recombination occurs between two recombinase recognition sites that are on the same molecule, the recombination reaction results in either the deletion or inversion of a sequence flanked by the two recognition sites. If a recombinase-mediated recombination occurs between two recombinase recognition sites that are on different molecules (e.g., between a recombinase recognition site on a target sequence and a recombinase recognition site on a donor sequence), the recombination reaction results in the insertion of a sequence from one of the molecules into the other molecule (e.g., the insertion of a donor sequence into a target molecule). When particular recognition sites that are capable of recombining are present on both the target and the donor (e.g., an attB site on the target and an attP site on the donor or an attL site on the target and an attR site on the donor), the recombination product represents an exchange of nucleotide sequence between the two sites, resulting in two new sites. Each of these new sites contains a part of the original recognition sites from both the donor and target molecules. For example, when recombination occurs between an attB site on the target and an attP site on the donor, attL and attR sites are created in the recombination products. Additionally, the newly formed attL and attR sites are flanked on one side by sequence obtained from the donor molecule and on the other side by sequence obtained from the target molecule.

"Regulatory element" includes a nucleotide sequence that is involved in conferring upon a host cell the expression of another nucleotide sequence, such as, for example, a sequence of interest. A regulatory element can comprise a promoter that is operably linked to the nucleotide sequence of interest and to a termination signal. Regulatory elements also typically encompass sequences useful for proper translation of the nucleotide sequence of interest.

"Selectable marker" or "selectable marker gene" refers to a nucleotide sequence whose expression in a cell gives the cell a selective advantage under particular conditions. The selective advantage possessed by the cell transformed with the selectable marker gene can be an improved ability to grow in the presence of a negative selective agent, such as an antibiotic or an herbicide, for example, as compared to the ability of non-transformed cells. Alternatively, the selective advantage possessed by the transformed cells can be an enhanced capacity, relative to non-transformed cells, to utilize a particular compound as a nutrient, growth factor, or energy source.

Alternatively, the selective advantage possessed by the transformed cell can be the loss of a previously possessed trait or characteristic, effecting what is termed "negative selection." In this last case, the host cell is exposed to or contacted by a compound that is toxic only to cells that have not lost the ability to express a specific trait or characteristic (such as a negative selectable marker gene, for example) that was present in the parent cell, which is typically a transgenic parent cell.

"Site-directed recombination" as used herein refers to recombination between two nucleotide sequences that each comprises at least one recognition site.

"Site-specific" means at a particular nucleotide sequence, which can be in a specific location in the genome of a host cell. The nucleotide sequence can be endogenous to the host cell, either in its natural location in the host genome or at some other location in the genome, or it can be a heterologous nucleotide sequence, which has been previously inserted into the genome of the host cell by any of a variety of known methods.

"Stably transformed" refers to a host cell that contains a nucleotide sequence of interest that has been stably integrated into the genome of the host cell.

"Target," "target molecule," "target sequence," and "target DNA" are used interchangeably to refer to a nucleotide sequence containing at least one recombinase recognition site. The target nucleotide sequence can be a gene, an expression cassette, a promoter, a molecular marker, a portion of any of these, or the like. The target sequence can be stably transformed into a cell to create a "target line" comprising the target sequence integrated into a chromosomal location in a genome.

A "targeted integration event" or "target event" refers to a recombination product formed between target and donor sequences in the presence of an integrase or integrase complex. In particular, it refers to the integration of a donor sequence into a target sequence as a consequence of an Int-mediated recombination when the target sequence is stably transformed into a cell.

A "visible marker gene" refers to a gene or nucleotide sequence whose expression in a transformed cell may not confer an advantage to that cell but can be detected or made visible. Examples of visible markers include, but are not limited to, β-glucuronidase (GUS), luciferase (LUC), and fluorescent proteins (such as green fluorescent protein (GFP) or cyan fluorescent protein (CFP), for example).

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, non-recited elements.

As used herein, the term "about", in the context of concentrations of components of the formulations, typically its means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be Understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered, to have speciﬁCally disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with, a proviso or negative limitation removing any subject matter from the genus, regardless of whether or not the excised material is specifically recited herein.

Disclosure of Optional Embodiments

Exemplary, non-limiting embodiments of a lambda integrase comprising at least one amino acid mutation at positions 43, 319 and 336, will now be disclosed.

In this context, mutations present in the lambda integrase described herein may comprise any mutations such as substitutions, deletions and also insertions of the natural amino acid sequence of the lambda integrase as long as the resulting polypeptide folds into a three-dimensionally stable structure and shows the desired (enhanced) recombination activity. The lambda integrase described herein may comprise conservative and/or non-conservative mutations: Examples of possible mutations are conservatively modified variations where the alteration is the substitution of an amino acid with a chemically similar amino acid. In addition to the above, the lambda integrase may comprise mutations, such as conservative mutations, outside of the regions as mentioned above. Such conservative substitutions are known to those of skill in the art and may include substitutions between: 1) alanine, serine, threonine; 2) aspartic acid and glutamic acid; 31 asparagine and glutamine; 4) arginine and lysine; 5) isoleucine, leucine, methionine, valine; and 6) phenylalanine, tyrosine, tyroptophan.

The "amino acid residue" as used herein refers to any amino acid and can either be in the D or L form or to an amine) acid mimetic that can be incorporated into a polypeptide by an amide bond.

Accordingly, the positively charged amino acid residue can for example either be a naturally occurring amino acid residue that is positively charged under physiological conditions such as arginine or lysine or a non-natural mimetic such as a lysine residue the alpha-amino group of which is alkylated in order to yield a (quarternary) ammonium-salt having a permanent positive charge.

In one embodiment a lambda integrase comprising at least one amino acid substitution at positions 43, 319 and 336 of the lambda integrase as set forth in SEQ ID NO: 1.

In another embodiment, the lambda integrase as described herein comprises an amino acid substitution at positions 43, 319 and 336 of the lambda integrase as set forth in SEQ ID NO: 1.

In another embodiment, the amino acid residue isoleucine at sequence position 43 is replaced by an aromatic amino acid. The aromatic amino acid may be selected from the group consisting of phenylalanine, tyrosine and tryptophan. In one embodiment the aromatic amino acid is phenylalanine.

In another embodiment, the amino acid residue glutamate at sequence position 319 is replaced by glycine.

In another embodiment, the amino acid residue aspartate at sequence position 336 may be replaced by a hydrophobic amino acid. The hydrophobic amino acid may be an aliphatic amino acid. The aliphatic amino acid may be selected from the group consisting of isoleucine, leucine and valine. In one embodiment the aliphatic amino acid is valine.

In a further embodiment, the lambda integrase as described herein may comprise the amino acid substitutions 143F, E319G and D336V.

In an alternative embodiment, the lambda integrase as described herein may comprise an amino acid substitution at position 336 of the lambda integrase as set forth in SEQ ID NO: 1. The amino acid residue aspartate at sequence position 336 may be replaced by a hydrophobic amino acid. The hydrophobic amino acid may be an aliphatic amino acid. The aliphatic amino acid may be selected from the group consisting of isoleucine, leucine and valine. In one embodiment, the aliphatic amino acid is valine.

The mutations in the lambda integrase as described herein are generally important in directing recombinase specificity and efficiency.

The lambda integrase as described herein can be generated through various selection systems known to persons skilled in the art. For example, bacterial selection systems relying on identification of functional mutants through reporter gene activation or substrate-linked protein evolution (SLiPE) have been previously described. These selection systems are one of many different approaches for engineering altered site-specificities in recombinases. For example, a genetic selection system in yeast has also been described that yielded HIV-1 integrase variants displaying altered DNA binding affinities. As another example, in vitro compartmentalization (IVC) can be used as a selection system for generating and identifying variants such as the mutants of the invention as described herein.

The bacteriophage lambda integrase is the prototypical member of the large tyrosine-recombinase family. Generally, the bacteriophage lambda integrase comprises 3 distinct domains that collaborate within a higher-order tetrameric structure to form a dynamic recombinogenic complex. These 3 domains are the N-terminal DNA binding domain (amino acid residues 1-64); the core DNA-binding domain (amino acid residues 65-175); and the C-terminal catalytic domain (amino acid residues 176-356). The bacteriophage lambda integrase is central to the bacteriophage lifecycle, facilitating the controlled integration and excision of its genome into and out of the host bacterial chromosome, respectively. In its natural function, the bacteriophage lambda integrase is able to catalyze site-specific recombination between a pair of target sequences, termed att sites, in the absence of high-energy cofactors. The target sequences (attP in the bacteriophage genome, attB in the bacterial genome) comprise a pair of 7 bp inverted core-binding sites separated by a 7 bp "overlap" region. The "overlap region" or "overlap sequence" as used herein defines the sequence of the recombination sequences where the DNA strand exchange, including strand cleavage and re-ligation, takes place and relates to the consensus DNA sequence 5'-TTTATAC-3' in wild-type att sites-or said sequence having functional nucleotide substitutions. The bacteriophage lambda integrase DNA core-binding domain primarily recognizes the 7 bp attP×attB core DNA sequence motifs. In the much longer attP site, the core sequence is flanked by binding sites for accessory DNA-bending factors such as integration host factor (IHF), factor for inversion stimulation (FIS) and excisionase (Xis). In addition to these accessory sites, several 'arm' binding sites for the N-terminal domain of the bacteriophage lambda integrase also flank the attP core site. Binding of the N-domain of the bacteriophage lambda integrase to 'arm' binding sites allosterically modulates the coupled core binding and catalytic domain to increase the affinity to core sites, which ultimately enables DNA strand cleavage and productive recombination of attB× attP. Therefore, these 'arm' regions are essential for activating efficient DNA cleavage by the C-terminal catalytic domain of bacteriophage lambda integrase, and thus contribute to the regulation of recombination directionality.

Generally, when a recombinase-mediated recombination occurs between two recognition sites, the recombination reaction can either occur on two different molecules or within the same molecule (e.g., between a recognition site on a target sequence and a recognition site on a donor sequence). In this context, the lambda integrase as described herein can catalyze either intermolecular or intramolecular recombination reactions or both intermolecular and intramolecular recombination reactions.

As used herein, "site-specific recombination" or "sequence-specific recombination" refers to recombination between two nucleotide sequences that each comprises at least one recognition site or at least one non-cognate site. "Site-specific" means at a particular nucleotide sequence, which can be in a specific location in the genome of a host cell for example. The nucleotide sequence can be endogenous to the host cell, either in its natural location in the host genome or at some other location in the genome, or it can be a heterologous nucleotide sequence, which has been previously inserted into the genome of the hose cell by any of a variety of known methods.

As described herein, "recognition sites" or "cognate sites" refer to a nucleotide sequence that can be recognized by a recombinase protein. The "recognition site" is the nucleotide sequence upon which binding, cleavage and strand exchange is performed by the recombinase protein and any associated accessory proteins. The lambda integrase recognizes cognate sites comprising attB, attP, attL, attR, and/or suitable mutations of such sites. The attB site and attP sites can be recombined together by the lambda integrase, or alternatively, the attL and attR sites can be recombined by the lambda integrase. In this context, the lambda integrase (Int mutants) described herein can facilitate recombination between, for example, the attB and attP sites. Advantageously, the lambda integrase described herein is able to recombine into non-cognate sites (such as the attH site) with greater efficiency, as compared to the parental Int-h/218 integrase.

In another embodiment there is provided a nucleic acid molecule comprising a nucleotide sequence encoding the lambda integrase as described herein.

It will be appreciated that the degeneracy of the genetic code permits substitutions of certain codons by other codons which specify the same amino acid and hence give rise to the same protein, the invention is not limited to a specific nucleic acid molecule but includes all nucleic acid molecules comprising a nucleotide sequence coding for the lambda integrase described herein.

In one embodiment, the nucleic acid molecule is operably linked to a regulatory sequence to permit expression of the nucleic acid molecule.

It will be appreciated that the precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of synthesis. Such regions will normally include non-coding regions which are located 5' and 3' to the nucleotide sequence to be expressed and which are involved with initiation of transcription and translation such as the TATA box, capping sequence and CAAT sequences. These regions can for example, also contain enhancer sequences or translated signal and leader sequences for targeting the produced polypeptide to a specific compartment of a host cell, which is used for producing a recombinant lambda integrase of the present invention. In one embodiment regulatory sequence comprises a promoter sequence.

In some embodiments, a nucleic acid of the invention comprises a transcriptional initiating region functional in a cell and a transcriptional terminating region functional in a cell. Suitable promoter sequences that can be used are for example, the lac promoter, the tet-promoter or the T7 promoter in the base pf bacterial expression. An example of a promoter suitable for expression in eukaryotic systems is the SV 40 promoter.

In further embodiments, the nucleic acid molecule is comprised in, a vector, particularly in an expression vector. Such an expression vector can comprise, besides the above-mentioned regulatory sequences and a nucleic acid sequence which codes for a lambda integrase, a sequence coding for restriction cleavage site Which adjoins the nucleic acid sequence coding for the lambda integrase it 5' and/or 3' direction. This vector also permits the introduction of another nucleic acid sequence coding for a protein to be expressed. The expression vector may also contain replication sites and control sequences derived from a species compatible with the host that is to be used for expression. The expression vector may be based on plasmids well known to person skilled in the art such as pBR322, puC16, pBluescript (®) and the like.

In one embodiment there is also provided a host cell containing a nucleic acid molecule. The vector containing the nucleic acid molecule can be transformed into host cells capable of expressing the genes. The transformation can be carried out in accordance with standard techniques. In this context, the transformed host cells can be cultured under conditions suitable for expression of the nucleotide sequence encoding the lambda integrase. Host cells can be established, adapted and completely cultivated under serum free conditions, and optionally in media which are free of any protein/peptide of animal origin. Commercially available media such as RPMI-1640 (Sigma), Dulbecco's Modified Eagle's Medium (DMEM; Sigma), Minimal Essential Medium (MEM; Sigma), CHO-S-SFMII (Invitrogen), serum free-CHO Medium (Sigma), and protein-free CHO Medium (Sigma) are exemplary appropriate nutrient solutions. Any of the media may be supplemented as necessary with a variety of compounds, examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that are known to those skilled in the art.

In yet another embodiment, there is provided a method of recombining a nucleic acid of interest into a target nucleic acid. The method comprises contacting a targeting nucleic acid comprising the nucleic acid of interest with the target nucleic acid in the presence of a lambda integrase as described herein.

In some embodiments, the method of recombining the nucleic acid of interest into the target nucleic acid is a sequence specific recombination. The sequence specific recombination can be performed in the presence of one or more cofactors. The cofactors can be selected from the group consisting of integration host factor (IHF), factor for inversion stimulation (FIS) and excisionase (Xis).

The "targeting nucleic acid" as used herein refers to a nucleotide sequence that contains at least one recognition site. The targeting nucleic acid can contact a target nucleic acid in the presence of a mutant of the invention, in order to recombine a nucleic acid of interest into the target nucleic acid. The targeting nucleotide sequence can be a gene, an expression cassette, a promoter, a molecular marker, a portion of any of the above, or the like. In some embodiments, the targeting nucleic acid can be a vector. In other embodiments, the targeting nucleic acid comprises a sequence selected from the group consisting of an attPH sequence (SEQ ID NO: 8) and an attP4X sequence (SEQ ID NO: 9). The term "nucleic acid of interest" as used herein refers to a polynucleotide sequence of any length that encodes a product of interest. The selected sequence can be a full length or a truncated gene, a fusion or tagged gene, and can be a cDNA, a genomic DNA, or a DNA fragment. It can also be the native sequence, i.e., naturally occurring form(s), or can be mutated or otherwise modified as desired. These modifications can include codon optimizations to optimize codon usage in the selected cell or host cell, humanization or tagging. The selected sequence can encode a secreted, cytoplasmic, nuclear, membrane bound or cell surface polypeptide. The "product of interest" can include, but are not limited to proteins, polypeptides, fragments thereof, peptides, antisense RNA, all of which can be produced in the selected host cell.

In one embodiment, the genomic DNA is comprised in a cell. The method described herein may be performed in all eukaryotic cells. Cells and cell lines may be present, for example in a cell culture and include but are not limited to eukaryotic cells, such as yeast, plant, insect or mammalian cells. For example, the cells may be oocytes, embryonic stem cells, hematopoietic stem cells or any type of differentiated cells. In certain embodiments, the method of the invention can be performed in a mammalian cell. The mammalian cell lines can include, but are not limited to a human, simian, murine, mice, rat, monkey, rabbit, rodent, hamster, goat, bovine, sheep or pig cell lines. Exemplary cell lines can include, but are not limited to Chinese hamster ovary (CHO) cells, murine myeloma cells such as NSO and Sp2/0 cells, COS cells, Hela cells and human embryonic kidney (HEK-293) cells.

The target nucleic acid may comprise DNA. The DNA may be genomic DNA.

In one embodiment, the target nucleic acid comprises a sequence selected from the group consisting of an attH sequence (SEQ ID: NO: 7) and an attH4X sequence (SEQ ID NO: 31). The targeting nucleic acid may be a vector. In one embodiment, the targeting nucleic acid comprises a sequence selected from the group consisting of an attH sequence (SEQ ID NO: 7) and am attH4X sequence (SEQ ID NO: 31).

In another embodiment sequence specific recombination may be performed in the presence of one or more cofactors. The cofactors may be selected from the group consisting of XIS, FIS and IHF.

In another embodiment, there is provided a sequence specific recombination kit comprising a targeting nucleic acid into which a nucleic acid of interest can be inserted, and lambda integrase or a nucleic acid as described herein.

The kit as described herein may comprise at least one reagent for inserting a nucleic of interest into the targeting nucleic acid. The reagent may be restriction enzyme or ligase. In another embodiment, the targeting nucleic acid may comprise a sequence selected from the group consisting of an attH sequence (SEQ ID NO: 7) and an attH4X sequence (SEQ ID NO: 31).

In one embodiment, the kit as described herein may further comprise buffer(s) and/or instructions for recombining the nucleic acid of interest with a given target nucleic acid.

In one embodiment, the kit as described herein may further comprise at least one reagent for determining successful sequence specific recombination event. In one embodiment, the reagent component is a primer pair. The primer pair may be supplied in combination with the kit or supplied separately from the kit.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 shows the sequence alignment of the core bacterial attB, and human attH and attH4X sequences. The 7 base pairs (bp) highlighted in grey represent the overlap sequence, which must be identical in both recombination partners, i.e. attB & attP, attH & attPH, attH4X and attP4X. The attH site differs from the bacterial attB site at one position in the 7 bp overlap sequence and three positions in the right arm core binding sequence. The non-cognate attH4X site occurs approximately 940 times in the human genome as part of human Line 1 (long interspersed nuclear elements/remnants of retrotransposons/non-coding). The first three nucleotides of the attH4X sequence are degenerate.

FIG. 3A shows in vivo recombination of exogenous DNA (lactamase gene cassette) into the attB site of E. coli chromosomal DNA mediated by integrase variant C3 as determined by PCR amplification from colonies growing on 100 ug/ML (1X) and 70 ug/mL (0.7X) ampicillin plates after being transformed with appropriate minicircles, described in FIG. 2. Chromosomal integration was verified using PCR primers flanking the endogenous attB site, etbliattBF (SEQ ID NO: 16) and ecoliattBR (SEQ ID NO: 17). In absence of integration, the expected PCR product is ~200 bp (as seen for colonies 1, 5, 6). Integration of the lactamase gene cassette results in a PCR product of ~1650 bp (colonies 2-4, 7-10).

FIG. 3B compares integration into attB of E. coli mediated by parental. Int-h/218 or C3 integrase. When parental Int-h/218 was used, only 2 colonies were observed (both of which, i.e. 100%, had correctly inserted lactamase cassette). In the case of C3, 27 colonies were observed. 10 of these were tested and 9 (90%) showed correctly inserted lactamase cassette. Therefore, of the 27 colonies, we can predict that ~90% (~24 colonies) contained the correctly inserted lactamase cassette. This corresponds to an improvement of ~12 fold (24 divided by 2).

FIG. 3C shows the nucleotide sequence of an integrant E. coli colony generated using C3 harboring the lactamase cassette. Bacterial chromosomal DNA flanking the cassette is in lower case. The attL and attR sites generated through recombination of attB and attP are underlined and in bold. The lactamase open reading frame is in bold.

FIG. 5A shows the intra-molecular recombination efficiency of the mutant integrases C2 without or with a C-terminal nuclear localization sequence (C2-N) of an episomal plasmid substrate in the HT1080 cell line with attB and attP sites. Y-axis denotes percentage eGFP positive cells (indicative of recombination between attB/attP sites) and activities are presented relative to the transfection efficiency as determined by EGFP vector transfection (100%). The mutant C2 recombined attB×attP more efficiently than Int-h/218.

FIG. 5B shows the intra-molecular recombination efficiency of the mutant integrases C2 without or with a C-terminal nuclear localization sequence (C2-N) of an episomal plasmid substrate in the HT1080 cell line with attH and attPH sites. Y-axis denotes percentage eGFP positive cells (indicative of recombination between attH/PH sites) and activities are presented relative to the transfection efficiency as determined by EGFP vector transfection (100%). The mutant C2 recombined attH and attPH more efficiently than Int-h/218.

FIG. 5C shows the intra-molecular recombination efficiency of the mutant integrases of an episomal plasmid substrate in the HT1080 cell line with attB and attP sites. Y-axis denotes percentage eGFP positive cells (indicative of recombination between attB/attP sites) and activities are presented relative to the transfection efficiency as determined by EGFP vector transfection (100%). The mutant C3 recombined attBxattP more efficiently than Int-h/218 or a codon-optimized Int-h/218 (opt Int).

FIG. 5D shows the intra-molecular recombination efficiency of the mutant integrase C3 of an episomal plasmid substrate in the HT1080 cell line, with attH and attPH sites. Y-axis denotes percentage eGFP positive cells (indicative of recombination between attH/PH sites) and activities are presented relative to the transfection efficiency as determined by EGFP vector transfection (100%) The mutant C3 recombined attH and attPH more efficiently than Int-h/218 or a codon-optimized Int-h/218 (opt Int).

FIG. 6B shows the nucleotide sequence of attL site generated through recombination between the attH4x and attP4x in the HT1080 clones 3 and 19. Human genomic DNA sequence flanking the attL sequence is in lower case. HOP' sequence is in italics, bold and underlined. The attL sequence is underlined and in bold. The PGK promoter sequence (part of the pPGKesPuro-attP4x targeting vector and driving the expression of Puromycin resistance gene) is in upper case. Genomic locus of the targeted attH4x sequence in each clone is specified.

EXAMPLES

Figure 2:
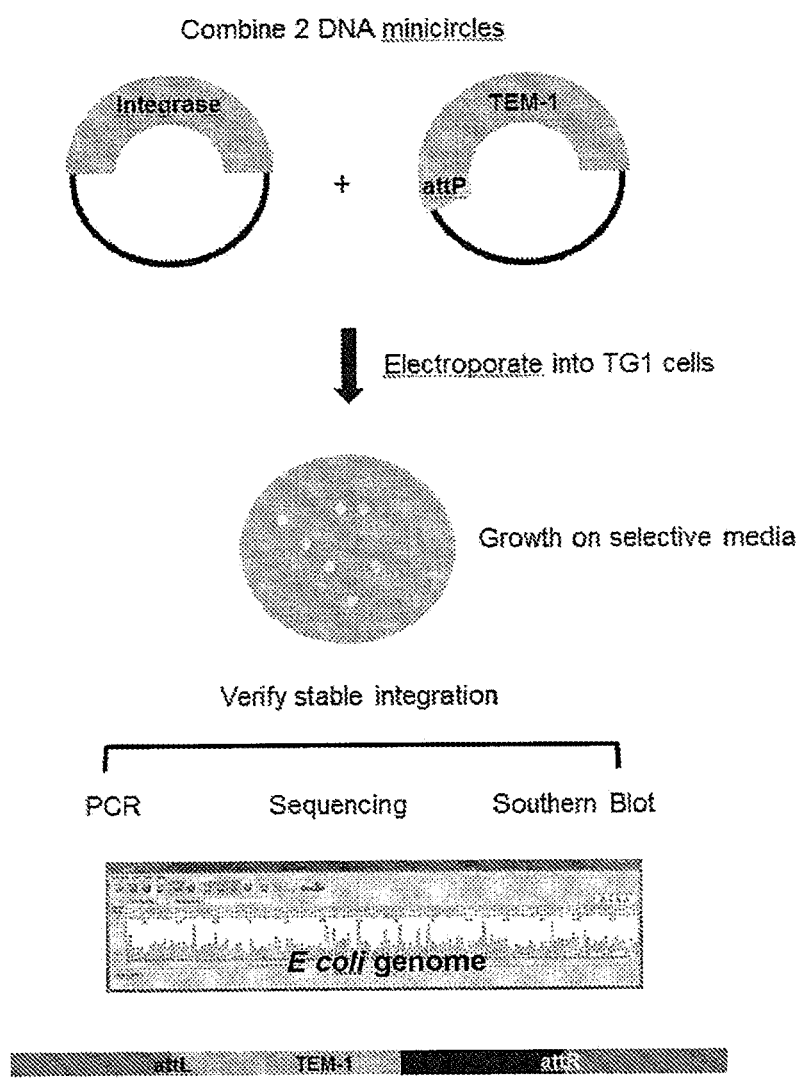
FIG. 2 shows the methodology for Rapid E. coli Chromosomal Integration using DNA minicircles and lambda integrase technology. The first step is to create a minicircle comprising lambda integrase under control of a suitable promoter (e.g. T7), and a minicircle comprising gene to be stably integrated, a selectable marker for antibiotic resistance (e.g. lactamase gene cassette) and the attP sequence. The second step is to transform both minicircles by electroporation or heat shock into E. coli, and then to plate and culture on selectable media (eg ampicillin plates). The third step is to confirm integration into attB site by PCR, sequencing and southern blot.

Non-limiting examples of the invention, including the best mode, and a comparative example will be further described in greater detail by reference to specific Examples, which should not be construed as in any way limiting the scope of the invention.

Materials

```
Int-h/218
                                                    SEQ ID NO: 1
MGRRRSHERRDLPPNLYIRNNGYYCYRDPRTGKEFGLGRDRRIAITEAIQANIELFSG

HKHKPLTARINSDNSVTLHSWLDRYEKILASRGIKQKTLINYMSKIKAIRRGLPDAPL

EDITTKEIAAMLNGYIDEGKAASAKLIRSTLSDAFREAIAEGHITTNHVAATRAAKSK

VRRSRLTADEYLKIYQAAESSPCWLRLAMELAVVTGQRVGDLCKMKWSDIVDGYLYVE

QSKTGVKIAIPTALHIDALGISMKETLDKCKEILGGETIIASTRREPLSSGTVSRYFM

RARKASGLSFEGDPPTFHELRSLSARLYEKQISDKFAQHLLGHKSDTMASQYRDDRGR

EWDKIEIK

C2 integrase mutant:
                                                    SEQ ID NO: 2
MGRRRSHERRDLPPNLYIRNNGYYCYRDPRTGKEFGLGRDRRIAITEAIQANIELFSG

HKHKPLTARINSDNSVTLHSWLDRYEKILASRGIKQKTLINYMSKIKAIRRGLPDAPL

EDITTKEIAAMLNGYIDEGKAASAKLIRSTLSDAFREAIAEGHITTNHVAATRAAKSK

VRRSRLTADEYLKIYQAAESSPCWLRLAMELAVVTGQRVGDLCKMKWSDIVDGYLYVE

QSKTGVKIAIPTALHIDALGISMKETLDKCKEILGGETIIASTRREPLSSGTVSRYFM

RARKASGLSFEGDPPTFHELRSLSARLYEKQISDKFAQHLLGHKSVTMASQYRDDRGR

EWDKIEIK

C3 integrase mutant:
                                                    SEQ ID NO: 3
MGRRRSHERRDLPPNLYIRNNGYYCYRDPRTGKEFGLGRDRRFAITEAIQANIELFSG

HKHKPLTARINSDNSVTLHSWLDRYEKILASRGIKQKTLINYMSKIKAIRRGLPDAPL

EDITTKEIAAMLNGYIDEGKAASAKLIRSTLSDAFREAIAEGHITTNHVAATRAAKSK

VRRSRLTADEYLKIYQAAESSPCWLRLAMELAVVTGQRVGDLCKMKWSDIVDGYLYVE

QSKTGVKIAIPTALHIDALGISMKETLDKCKEILGGETIIASTRREPLSSGTVSRYFM

RARKASGLSFEGDPPTFHELRSLSARLYGKQISDKFAQHLLGHKSVTMASQYRDDRGR

EWDKIEIK
```

-continued

Lambda integrase:
SEQ ID NO: 4
ATGGGAAGAAGGCGAAGTCATGAGCGCCGGGATTTACCCCCTAACCTTTATATAAGAA

ACAATGGATATTACTGCTACAGGGACCCAAGGACGGGTAAAGAGTTTGGATTAGGCAG

AGACAGGCGAATCGCAATCACTGAAGCTATACAGGCCAACATTGAGTTATTTTCAGGA

CACAAACACAAGCCTCTGACAGCGAGAATCAACAGTGATAATTCCGTTACGTTACATT

CATGGCTTGATCGCTACGAAAAAATCCTGGCCAGCAGAGGAATCAAGCAGAAGACACT

CATAAATTACATGAGCAAAATTAAAGCAATAAGGAGGGGTCTGCCTGATGCTCCACTT

GAAGACATCACCACAAAAGAAATTGCGGCAATGCTCAATGGATACATAGACGAGGGCA

AGGCGGCGTCAGCCAAGTTAATCAGATCAACACTGAGCGATGCATTCCGAGAGGCAAT

AGCTGAAGGCCATATAACAACAAACCATGTCGCTGCCACTCGCGCAGCAAAATCAAAG

GTAAGGAGATCAAGACTTACGGCTGACGAATACCTGAAAATTTATCAAGCAGCAGAAT

CATCACCATGTTGGCTCAGACTTGCAATGGAACTGGCTGTTGTTACCGGGCAACGAGT

TGGTGATTTATGCAAAATGAAGTGGTCTGATATCGTAGATGGATATCTTTATGTCGAG

CAAAGCAAAACAGGCGTAAAAATTGCCATCCCAACAGCATTGCATATTGATGCTCTCG

GAATATCAATGAAGGAAACACTTGATAAATGCAAAGAGATTCTTGGCGGAGAAACCAT

AATTGCATCTACTCGTCGCGAACCGCTTTCATCCGGCACAGTATCAAGGTATTTTATG

CGCGCACGAAAAGCATCAGGTCTTTCCTTCGAAGGGGATCCGCCTACCTTTCACGAGT

TGCGCAGTTTGTCTGCAAGACTCTATGAGAAGCAGATAAGCGATAAGTTTGCTCAACA

TCTTCTCGGGCATAAGTCGGACACCATGGCATCACAGTATCGTGATGACAGAGGCAGG

GAGTGGGACAAAATTGAAATCAAATAA attB:
SEQ ID NO: 5
CTGCTTTTTT ATACTAACTT G attP:
SEQ ID NO: 6
CAGCTTTTTT ATACTAAGTT G attH:
SEQ ID NO: 7
CTGCTTTCTT ATACCAAGTG G attPH:
SEQ ID NO: 8
CAGCTTTCTT ATACCAAGTT G attP4X:
SEQ ID NO: 9
CAGCTTTATT TCATTAAGTT G petF2:
SEQ ID NO: 10
CATCGGTGATGTCGGCGAT petR:
SEQ ID NO: 11
CGGATATAGTTCCTCCTTTCAGCA attP-F:
SEQ ID NO: 12
cacagaattcCGT CTG TTA CAG GTC ACT AAT ACC ATC T attPSOE-R:
SEQ ID NO: 13
ACA TTT CCC CGA AAA GTG CCA CCT GAA CAT CAC CGG GAA ATC AAA TAA TGA T TEM1prom-F:
SEQ ID NO: 14
TTC AGG TGG CAC TTT TCG GGG AAA TGT -continued TEM1prom-R:
SEQ ID NO: 15
TGT GGA ATT CCT ACA CTA GAA GGA CAG TAT TTG GTA TCT GC EcoliAttB-F:
SEQ ID NO: 16
CTG AAA ATG TGT TCA CAG GTT GCT EcoliattB-R:
SEQ ID NO: 17
GCA ATG CCA TCT GGT ATC ACT C2 gene sequence:
SEQ ID NO: 18
ATGGGAAGAAGGCGAAGTCATGAGCGCCGGGATTTACCCCCTAACCTTTATATAAGAA

ACAATGGATATTACTGCTACAGGGACCCAAGGACGGGTAAAGAGTTTGGATTAGGCAG

AGACAGGCGAATCGCAATCACTGAAGCTATACAGGCCAACATTGAGTTATTTTCAGGA

CACAAACACAAGCCTCTGACAGCGAGAATCAACAGTGATAATTCCGTTACGTTACATT

CATGGCTTGATCGCTACGAAAAAATCCTGGCCAGCAGAGGAATCAAGCAGAAGACACT

CATAAATTACATGAGCAAAATTAAAGCAATAAGGAGGGGTCTGCCTGATGCTCCACTT

GAAGACATCACCACAAAAGAAATTGCGGCAATGCTCAATGGATACATAGACGAGGGCA

AGGCGGCGTCAGCCAAGTTAATCAGATCAACGCTGAGCGATGCATTCCGAGAGGCAAT

AGCTGAAGGCCATATAACAACAAACCATGTCGCTGCCACTCGCGCAGCAAAGTCAAAG

GTAAGGAGATCAAGACTTACGGCTGACGAATACCTGAAAATTTATCAAGCAGCAGAAT

CATCACCATGTTGGCTCAGACTTGCAATGGAACTGGCTGTTGTTACCGGGCAACGAGT

TGGTGACTTGTGCAAAATGAAGTGGTCTGATATCGTAGATGGATATCTTTATGTCGAG

CAAAGCAAAACAGGCGTAAAAATTGCCATCCCAACAGCATTGCATATTGATGCTCTCG

GAATATCAATGAAGGAAACACTTGATAAATGCAAAGAGATTCTTGGCGGAGAAACCAT

AATTGCATCTACTCGTCGCGAACCGCTTTCATCCGGCACAGTATCAAGGTATTTTATG

CGCGCACGAAAAGCATCAGGTCTTTCCTTCGAAGGGGATCCGCCTACCTTTCACGAGT

TGCGCAGTTTGTCTGCAAGACTCTATGAGAAGCAGATAAGCGATAAGTTTGCTCAACA

TCTTCTCGGGCATAAGTCGGTCACCATGGCATCACAGTATCGTGATGACAGAGGCAGG

GAGTGGGACAAAATTGAAATCAAATAA

C3 gene sequence:
SEQ ID NO: 19
ATGGGAAGAAGGCGAAGTCATGAGCGCCGGGATTTACCCCCTAACCTTTATATAAGAA

ACAATGGATATTACTGCTACAGGGACCCAAGGACGGGTAAAGAGTTTGGATTAGGCAG

AGACAGGCGATTCGCAATCACTGAAGCTATACAGGCCAACATTGAGTTATTTTCAGGA

CACAAACACAAGCCTCTGACAGCGAGAATCAACAGTGATAATTCCGTTACGTTACATT

CATGGCTTGATCGCTACGAAAAAATCCTGGCCAGCAGAGGAATCAAGCAGAAGACACT

CATAAATTACATGAGCAAAATTAAAGCAATAAGGAGGGGTCTGCCTGATGCTCCACTT

GAAGACATCACCACAAAAGAAATTGCGGCAATGCTCAATGGATACATAGACGAGGGCA

AGGCGGCGTCAGCCAAGTTAATCAGATCAACGCTGAGCGATGCATTCCGAGAGGCAAT

AGCTGAAGGCCATATAACAACAAACCATGTCGCTGCCACTCGCGCGGCAAAGTCAAAG

GTAAGGAGATCAAGACTTACGGCTGACGAATACCTGAAAATTTATCAAGCAGCAGAAT

CATCACCATGTTGGCTCAGACTTGCAATGGAACTGGCTGTTGTTACCGGGCAACGAGT

TGGTGACTTGTGCAAAATGAAGTGGTCTGATATCGTAGATGGATATCTTTATGTCGAG

CAAAGCAAAACAGGCGTAAAAATTGCCATCCCAACAGCATTGCATATTGATGCTCTCG

```
GAATATCAATGAAGGAAACACTTGATAAATGCAAAGAGATTCTTGGCGGAGAAACCAT

AATTGCATCTACTCGTCGCGAACCGCTCTCATCCGGCACAGTATCAAGGTATTTTATG

CGCGCACGAAAAGCATCAGGTCTTTCCTTCGAAGGGGATCCGCCTACCTTTCACGAGT

TGCGCAGTTTGTCTGCAAGACTCTATGGGAAGCAGATAAGCGATAAGTTTGCTCAACA

TCTTCTCGGGCATAAGTCGGTCACCATGGCATCACAGTATCGTGATGACAGAGGCAGG

GAGTGGGACAAAATTGAAATCAAATAA
```

C3 minicircle:

SEQ ID NO: 20
```
CATCGGTGATGTCGGCGATATAGGCGCCAGCAACCGCACCTGTGGCGCCGGTGATGCC

GGCCACGATGCGTCCGGCGTAGAGGATCGAGATCTCGATCCCGCGAAATTAATACGAC

TCACTATAGGGGAATTGTGAGCGGATAACAATTCCCCTCTAGAAATAATTTTGTTTAA

CTTTAAGAAGGAGATATACATATGGGAAGAAGGCGAAGTCATGAGCGCCGGGATTTAC

CCCCTAACCTTTATATAAGAAACAATGGATATTACTGCTACAGGGACCCAAGGACGGG

TAAAGAGTTTGGATTAGGCAGAGACAGGCGATTCGCAATCACTGAAGCTATACAGGCC

AACATTGAGTTATTTTCAGGACACAAACACAAGCCTCTGACAGCGAGAATCAACAGTG

ATAATTCCGTTACGTTACATTCATGGCTTGATCGCTACGAAAAAATCCTGGCCAGCAG

AGGAATCAAGCAGAAGACACTCATAAATTACATGAGCAAAATTAAAGCAATAAGGAGG

GGTCTGCCTGATGCTCCACTTGAAGACATCACCACAAAAGAAATTGCGGCAATGCTCA

ATGGATACATAGACGAGGGCAAGGCGGCGTCAGCCAAGTTAATCAGATCAACGCTGAG

CGATGCATTCCGAGAGGCAATAGCTGAAGGCCATATAACAACAAACCATGTCGCTGCC

ACTCGCGCGGCAAAGTCAAAGGTAAGGAGATCAAGACTTACGGCTGACGAATACCTGA

AAATTTATCAAGCAGCAGAATCATCACCATGTTGGCTCAGACTTGCAATGGAACTGGC

TGTTGTTACCGGGCAACGAGTTGGTGACTTGTGCAAAATGAAGTGGTCTGATATCGTA

GATGGATATCTTTATGTCGAGCAAAGCAAAACAGGCGTAAAAATTGCCATCCCAACAG

CATTGCATATTGATGCTCTCGGAATATCAATGAAGGAAACACTTGATAAATGCAAAGA

GATTCTTGGCGGAGAAACCATAATTGCATCTACTCGTCGCGAACCGCTCTCATCCGGC

ACAGTATCAAGGTATTTTATGCGCGCACGAAAAGCATCAGGTCTTTCCTTCGAAGGGG

ATCCGCCTACCTTTCACGAGTTGCGCAGTTTGTCTGCAAGACTCTATGGGAAGCAGAT

AAGCGATAAGTTTGCTCAACATCTTCTCGGGCATAAGTCGGTCACCATGGCATCACAG

TATCGTGATGACAGAGGCAGGGAGTGGGACAAAATTGAAATCAAACATCATCACCATC

ACCACTAATGAGAATTCgagctccgtcgacaagcttgcggccgcactcgagcaccacc accaccaccactgagatccggctgctaacaaagcccgaaaggaagctgagttggctgc tgccaccgctgagcaataactagcataaccccttggggcctctaaacgggtcttgagg ggttttttgctgaaaggaggaactatatccg
``` attP-TEM1:

SEQ ID NO: 21
```
cacagaattcCGtctgttacaggtcactaataccatctaagtagttgattcatagtga ctgcatatattgtgttttacagtattatgtagtctgtttttttatgcaaaatctaattt aatatattgatatttatatcattttacgtttctcgttcagcttttttatactaagttg gcattataaaaaagcattgcttatcaatttgttgcaacgaacaggtcactatcagtca aaataaaatcattatttgATTTCCCGGTGATGttcaggtggcacttttcggggaaatg tgcgcggaacccctatttgtttattttttctaaatacattcaaatatgtatccgctcat gagacaataaccctgataaatgcttcaataatattgaaaaaggaagagtatgagtatt
```

-continued caacatttccgtgtcgcccttattccctttttttgcggcattttgccttcctgtttttg ctcacccagaaacgctggtgaaagtaaaagatgctgaagatcagttgggtgcacgagt gggttacatcgaactggatctcaacagcggtaagatccttgagagttttcgccccgaa gaacgttttccaatgatgagcacttttaaagttctgctatgtggcgcggtattatccc gtattgacgccgggcaagagcaactcggtcgccgcatacactattctcagaatgactt ggttgagtactcaccagtcacagaaaagcatcttacggatggcatgacagtaagagaa ttatgcagtgctgccataaccatgagtgataacactgcggccaacttacttctgacaa cgatcggaggaccgaaggagctaaccgcttttttgcacaacatgggggatcatgtaac tcgccttgatcgttgggaaccggagctgaatgaagccataccaaacgacgagcgtgac accacgatgcctgcagcaatggcaacaacgttgcgcaaactattaactggcgaactac ttactctagcttcccggcaacaattaatagactggatggaggcggataaagttgcagg accacttctgcgctcggcccttccggctggctggtttattgctgataaatctggagcc ggtgagcgtgggtctcgcggtatcattgcagcactggggccagatggtaagccctccc gtatcgtagttatctacacgacggggagtcaggcaactatggatgaacgaaatagaca gatcgctgagataggtgcctcactgattaagcattggtaactgtcagaccaagtttac tcatatactttagattgatttaaaacttcattttaatttaaaaggatctaggtga agatcctttttgataatctcatgaccaaaatcccttaacgtgagttttcgttccactg agcgtcagaccccgtagaaaagatcaaaggatcttcttgagatcctttttttctgcgc gtaatctgctgcttgcapacaaaaaaaccaccgctaccagcggtggtttgtttgccgg atcaagagctaccaactctttttccgaaggtaactggcttcagcagagcgcagatacc aaatactgtccttctagtgtagccgtagttagg

HOP':
SEQ ID NO: 22
ATGCTTTATTTCATTAAGTTG attL:
SEQ ID NO: 23
GCATTATAAAAAAGCATTGCTTATCAATTTGTTGCAACGAACAGGTCACTATC
AGTCAAAATACAATCATTATTTGATTTCAATTTTGTCCCACTCCCTCCCG PGK promoter:
SEQ ID NO: 24
AATTCTACCGGGTAGGGGAGGCGCTTTTCCCAAGGCAGTCTGGAGCATGCGCTTTAGC

AGCCCCGCTGGGCACTTGGCGCTACACAAGTGGCCTCTGGCCTCGCACACATTCCACA

TCCACCGGTAGGCGCCAACCGGCTCCGTTCTTTGGTGGCCCCTTCGCGCCACCTTCTA

CTCCTCCCCTAGTCAGGAAGTTCCCCCCCGCCCCGCAGCTCGCGTCGTGCAGGACGTG

ACAAATGGAAGTAGCACGTCTCACTAGTCTCGTGCAGATGGACAGCACCGCTGAGCAA

TGGAAGCGGGTAGGCCTTTGGGGCAGCGGCCAATAGCAGCT

HOP' attH4X_F1:
SEQ ID NO: 25
GAGTGTTTTCCAACTTGGTTCCATT

PuroRev24:
SEQ ID NO: 26
CACCGTGGGCTTGTACTCGGTC pLIR-F1:
SEQ ID NO: 27
CTGCATCGATTCAGCTAGCTG pLIR-R1:
SEQ ID NO: 28
CTGATAGTGACCTGTTCGTTGC -continued pPGKssPuro-attP4x (targeting vector):
SEQ ID NO: 29
gaattcctctgttacaggtcactaataccatctaagtagttgattcatagtgactgca tatgttgtgttttacagtattatgtagtctgttttttatgcaaaatctaatttaatat attgatatttatatcattttacgtttctcgttcagctttatttcattaagttggcatt ataaaaaagcattgcttatcaatttgttgcaacgaacaggtcactatcagtcaaaata aaatcattatttgatttcaattttgtcccactccctcccgaattctaccgggtagggg aggcgcttttcccaaggcagtctggagcatgcgctttagcagccccgctggcacttgg cgctacacaagtggcctctggcctcgcacacattccacatccaccggtagcgccaacc ggctccgttctttggtggccccttcgcgccacttctactcctcccctagtcaggaagt ttcccccccgccccgcagctcgcgtcgtgcaggacgtgacaaatggaagtagcacgtc tcactagtctcgtgcagatggacagcaccgctgagcaatggaagcgggtaggcctttg gggcagcggccaatagcagctttgctccttcgctttctgggctcagaggctgggaagg ggtgggtccgggggcgggctcaggggcgggctcaggggcggggcgggcgcccgaaggt cctccggaggcccggcattctgcacgcttcaaaagcgcacgtctgccgcgcgctgttctc ctcttcctcatctccgggcctttcgaccaattcgctgtctgcgagggccagctgttgg ggtgagtactccctctcaaaagcgggcatgacttctgcgctaagattgtcagtttcca aaaacgaggaggatttgatattcacctggcccgcggtgatgcctttgagggtggccgc gtccatctggtcagaaaagacaatcttttgttgtcaagcttgaggtgtggcaggctt gagatctggccatacacttgagtgacaatgacatccactttgcctttctctccacagg tgtccactcccaggtccaactgcagatgaccgagtacaagcccacggtgcgcctcgcc acccgcgacgacgtcccccgggccgtacgcaccctcgccgccgcgttcgccgactacc ccgccacgcgccacaccgtcgacccggaccgccacatcgagcgggtcaccgagctgca agaactcttcctcacgcgcgtcgggctcgacatcggcaaggtgtgggtcgcggacgac ggcgccgcggtggcggtctggaccacgccggagagcgtcgaagcgggggcggtgttcg ccgagatcggcccgcgcatggccgagttgagcggttcccggctggccgcgcagcaaca gatggaaggcctcctggcgccgcaccggcccaaggagcccgcgtggttcctggccacc gtcggcgtctcgcccgaccaccagggcaagggtctgggcagcgccgtcgtgctccccg gagtggaggcggccgagcgcgccggggtgcccgccttcctggagacctccgcgccccg caacctccccttctacgagcggctcggcttcaccgtcaccgccgacgtcgaggtgccc gaaggaccgcgcacctggtgcatgacccgcaagcccggtgcctgatctagagctcgct gatcagcctcgactgtgccttctagttgccagccatctgttgtttgcccctcccccgt gccttccttgaccctggaaggtgccactcccactgtcctttcctaataaaatgaggaa attgcatcgcattgtctgagtaggtgtcattctattctggggggtggggtggggcagg acagcaaggggaggattgggaagacaatagcaggcatgctggggctgcggtgggctc tatggcttctgaggcggaaagaaccagctggggctcgagatccactagttctaggctc gaggctagagcggccgccaccgcggtggagctccaattcgccctatagtgagtcgtat tacgcgcgctcactggccgtcgttttacaacgtcgtgactgggaaaaccctggcgtta cccaacttaatcgccttgcagcacatccccctttcgccagctggcgtaatagcgaaga ggcccgcaccgatcgcccttcccaacagttgcgcagcttgaatggcgaatgggacgcg ccctgtagcggcgcattaagcgcggcgggtgtggtggttacgcgcagcgtgaccgcta -continued

```
cacttgccagcgccctagcgcccgctccttcgctttcttcccttcctttctcgccac
gttcgccggctttccccgtcaagctctaaatcggggctcccttagggttccgattt
agtgctttacggcacctcgaccccaaaaaacttgattagggtgatggttcacgtagtg
ggccatcgccctgatagacggttttcgccctttgacgttggagtccacgttctttaa
tagtggactcttgttccaaactggaacaacactcaabcctatctcggtctattcttt
gatttataagggattttgacgatttcggcctattggttaaaaaatgagctgatttaac
aaaaatttaacgcgaattttaacaaaatattaacgcttacaatttaggtggcactttt
cggggaaatgtgcgcggaaccccctatttgtttatttttctaaatacattcaaatatgt
atccgctcatgagacaataaccctgataaatgcttcaataatattgaaaaaggaagag
tatgagtattcaacatttccgtgtcgcccttattccattttttgcggcatttttgcctt
cctgttttttgctcacccagaaacgatggtgaaagtaaaagatgctgaagatcagttgg
gtgcacgagtgggttacatcgaactggatctcaacagcggtaagatccttgagagttt
tcgccccgaagaacgttttccaatgatgagcacttttaaagttctgctatgtggcgcg
gtattatcccgtattgacgccgggcaagagcaactcggtcgccgcatacactattctc
agaatgacttggttgagtactcaccagtcacagaaaagcatcttacggatggcatgac
agtaagagaattatgcagtgctgccataaccatgagtgataacactgcggccaactta
cttctgacaacgatcggaggaccgaaggagctaaccgcttttttgcacaacatgggg
atcatgtaactcgccttgatcgttgggaaccggagctgaatgaagccataccaaacga
cgagcgtgacaccacgatgcctgtagcaatggcaacaacgttgcgcaaactattaact
ggcgaaatacttactctagcttcccggcaacaattaatagactggatggaggcggata
aagttgcaggaccacttctgcgctcggcccttccggctggctggtttattgctgataa
atctggagccggtgagcgtgggtctcgcggtatcattgcagcactggggccagatggt
aagcccctcccgtatcgtagttatctacacgacggggagtcaggcaactatggatgaac
gaaatagacagatcgctgagataggtgcctcactgattaagcattggtaactgtcaga
ccaagtttactcatatatactttagattgatttaaaacttcattttaatttaaaagg
atctaggtgaagatcctttttgataatctcatgaccaaaatcccttaacgtgagtttt
cgttccactgagcgtcagacccgtagaaaagatcaaaggatcttcttgagatccttt
ttttctgcgcgtaatctgctgcttgcaaacaaaaaaaccaccgctaccagcggtggtt
tgtttgccggatcaagagctaccaactcttttttccgaaggtaactggcttcagcagag
cgcagataccaaatactgtccttctagtgtagccgtagttaggccaccacttcaagaa
ctctgtagcaccgcctacatacctcgctctgctaatcctgttaccagtggctgctgcc
agtggcgataagtcgtgtcttaccgggttggactcaagacgatagttaccggataagg
cgcagcggtcgggctgaacggggggttcgtgcacacagcccagcttggagcgaacgac
ctacaccgaactgagatacctacagcgtgagctatgagaaagcgccacgcttcccgaa
gggagaaaggcggacaggtatccggtaagcggcagggtcggaacaggagagcgcacga
gggagcttccagggggaaacgcctggtatctttatagtcctgtcgggtttcgccacct
ctgacttgagcgtcgatttttgtgatgctcgtcaggggggcggagcctatggaaaaac
gccagcaacgcggcctttttacggttcctggccttttgctggccttttgctcacatgt
tctttcctgcgttatcccctgattctgtggataaccgtattaccgcctttgagtgagc
tgataccgctcgccgcagccgaacgaccgagcgcagcgagtcagtgagcgaggaagcg
gaagagcgcccaatacgcaaaccgcctctccccgcgcgttggccgattcattaatgca
```

-continued

```
gctggcacgacaggtttcccgactggaaagcgggcagtgagcgcaacgcaattaatgt
gagttagctcactcattaggcaccccaggctttacactttatgcttccggctcgtatg
ttgtgtggaattgtgagcggataacaatttcacacaggaaacagctatgaccatgatt
acgccaagcgcgcaattaaccctcactaaagggaacaaaagctgggtaccgggcccccc
cctcgaggtcgacggtatcgataagcttgatatc
``` pCMVssKZ-IntC3-CNLS (the integrase expression plasmid):

SEQ ID NO: 30

```
gaattcctcacatgttctttcctgcgttatcccctgattctgtggataaccgtattac
cgccatgcattagttattaatagtaatcaattacggggtcattagttcatagcccata
tatggagttccgcgttacataacttacggtaaatggcccgcctggctgaccgcccaac
gacccccgcccattgacgtcaataatgacgtatgttcccatagtaacgccaataggga
ctttccattgacgtcaatgggtggagtatttacggtaaactgcccacttggcagtaca
tcaagtgtatcatatgccaagtacgccccctattgacgtcaatgacggtaaatggccc
gcctggcattatgcccagtacatgaccttatgggactttcctacttggcagtacatct
acgtattagtcatcgctattaccatggtgatgcggttttggcagtacatcaatgggcg
tggatagcggtttgactcacggggatttccaagtctccaccccattgacgtcaatggg
agtttgttttggcaccaaaatcaacgggactttccaaaatgtcgtaacaactccgccc
cattgacgcaaatgggcggtaggcgtgtacggtgggaggtctatataagcagagctgg
tttagtgaaccgtcagatccgctagcaattcgctgtctgcgagggccagctgttgggg
tgagtactccctctcaaaagcgggcatgacttctgcgctaagattgtcagtttccaaa
aacgaggaggatttgatattcacctggcccgcggtgatgcctttgagggtggccgcgt
ccatctggtcagaaaagacaatcttttgttgtcaagcttgaggtgtggcaggcttga
gatctggccatacacttgagtgacaatgacatccactttgcctttctctccacaggtg
tccactcccaggtccaactgcagctcgaggtccaccatgggaagaaggcgaagtcatg
agcgccgggatttaccccctaacctttatataagaaacaatggatattactgctacag
ggacccaaggacgggtaaagagtttggattaggcagagacaggcgattcgcaatcact
gaagctatacaggccaacattgagttattttcaggacacaaacacaagcctctgacag
cgagaatcaacagtgataattccgttacgttacattcatggcttgatcgctacgaaaa
aatcctggccagcagaggaatcaagcagaagacactcataaattacatgagcaaaatt
aaagcaataaggaggggtctgcctgatgctccacttgaagacatcaccacaaaagaaa
ttgcggcaatgctcaatggatacatagacgagggcaaggcggcgtcagccaagttaat
cagatcaacgctgagcgatgcattccgagaggcaatagctgaaggccatataacaaca
aaccatgtcgctgccactcgcgeggcaaagtcaaaggtaaggagatcaagacttacgg
ctgacgaatacctgaaaatttatcaagcagcagaatcatcaccatgttggctcagact
tgcaatggaactggctgttgttaccgggcaacgagttggtgacttgtgcaaaatgaag
tggtctgatatcgtagatggatatctttatgtcgagcaaagcaaaacaggcgtaaaaa
ttgccatcccaacagcattgcatattgatgctctcggaatatcaatgaaggaaacact
tgataaatgcaaagagattcttggcggagaaaccataattgcatctactcgtcgcgaa
ccgctctcatccggcacagtatcaaggtatttatgcgcgcacgaaaagcatcaggtc
tttccttcgaaggggatccgcctacctttcacgagttgcgcagtttgtctgcaagact
ctatgggaagcagataagcgataagtttgctcaacatcttctcgggcataagtcggtc
```

-continued

```
accatggcatcacagtatcgtgatgacagaggcagggagtgggacaaaattgaaatca aatccggaggcggccctaagaagaagagaaaggtatgataatctagagctcgctgatc agcctcgactgtgccttctagttgccagccatctgttgtttgccctccccgtgcct tccttgaccctggaaggtgccactcccactgtcctttcctaataaaatgaggaaattg catcgcattgtctgagtaggtgtcattctattctgggggtggggtggggcaggacag caaggggaggattgggaagacaatagcaggcatgctggggatgcggtgggctctatg gcttctgaggcggaaagaaccagctggggctcgagatccactagttctagcctcgagg ctagagcggccgccaccgcggtggagctccaattcgccctatagtgagtcgtattacg cgcgctcactggccgtcgttttacaacgtcgtgactgggaaaaccctggcgttaccca acttaatcgccttgcagcacatcccccttcgCcagctggcgtaatagcgaagaggcc cgcaccgatcgcccttcccaacagttgcgcagcctgaatggcgaatgggacgcgccct gtagcggcgcattaagcgcggcgggtgtggtggttacgcgcagcgtgaccgctacact tgccagcgccctagcgcccgctcctttcgctttcttcccttcctttctcgccacgttc gccggctttccccgtcaagctctaaatcgggggctccctttagggttccgatttagtg ctttacggcacctcgaccccaaaaaacttgattagggtgatggttcacgtagtgggcc atcgccctgatagacggtttttcgccctttgacgttggagtccacgttctttaatagt ggactcttgttccaaactggaacaacactcaaccctatctcggtctattcttttgatt tataagggattttgccgatttcggcctattggttaaaaaatgagctgatttaacaaaa atttaacgcgaattttaacaaaatattaacgcttacaatttaggtggcacttttcggg gaaatgtgcgcggaaccctatttgtttatttttctaaatacattcaaatatgtatcc gctcatgagacaataaccctgataaatgcttcaataatattgaaaaaggaagagtatg agtattcaacatttccgtgtcgcccttattccctttttgcggcattttgccttcctg ttttgctcacccagaaacgctggtgaaagtaaaagatgctgaagatcagttgggtgc acgagtgggttacatcgaactggatctcaacagcggtaagatccttgagagttttcgc cccgaagaacgttttccaatgatgagcacttttaaagttctgctatgtggcgcggtat tatcccgtattgacgccgggcaagagcaactcggtcgccgcatacactattctcagaa tgacttggttgagtactcaccagtcacagaaaagcatcttacggatggcatgacagta agagaattatgcagtgctgccataaccatgagtgataacactgcggccaacttacttc tgacaacgatcggaggaccgaaggagctaaccgcttttttgcacaacatggggatca tgtaactcgccttgatcgttgggaaccggagctgaatgaagccataccaaacgacgag cgtgacaccacgatgcctgtagcaatggcaacaacgttgcgcaaactattaactggcg aactacttactctagcttcccggcaacaattaatagactggatggaggcggataaagt tgcaggaccacttctgcgctcggcccttccggctggctggtttattgctgataaatct ggagccggtgagcgtgggtctcgcggtatcattgcagcactggggccagatggtaagc cctcccgtatcgtagttatctacacgacggggagtcaggcaactatggatgaacgaaa tagacagatcgctgagataggtgcctcactgattaagcattggtaactgtcagaccaa gtttactcatatatactttagattgatttaaaacttcattttttaatttaaaaggatct aggtgaagatcctttttgataatctcatgaccaaaatcccttaacgtgagttttcgtt ccactgagcgtcagaccccgtagaaaagatcaaaggatcttcttgagatcctttttt ctgcgcgtaatctgctgcttgcaaacaaaaaaaccaccgctaccagcggtggtttgtt tgccggatcaagagctaccaactctttttccgaaggtaactggcttcagcagagcgca
```

```
gataccaaatactgtccttctagtgtagccgtagttaggccaccacttcaagaactct gtagcaccgcctacatacctcgctctgctaatcctgttaccagtggctgctgccagtg gcgataagtcgtgtcttaccgggttggactcaagacgatagttaccggataaggcgca gcggtcgggctgaacgggggttcgtgcacacagcccagcttggagcgaacgacctac accgaactgagatacctacagcgtgagctatgagaaagcgccacgcttcccgaaggga gaaaggcggacaggtatccggtaagcggcagggtcggaacaggagagcgcacgaggga gcttccaggggggaaacgcctggtatctttatagtcctgtcgggtttcgccacctctga cttgagcgtcgattttgtgatgctcgtcagggggcggagcctatggaaaaacgcca gcaacgcggccttttacggttcctggccttttgctggccttttgctcacatgttctt tcctgcgttatcccctgattctgtggataaccgtattaccgcctttgagtgagctgat accgctcgccgcagccgaacgaccgagcgcagcgagtcagtgagcgaggaagcggaag agcgcccaatacgcaaaccgcctctccccgcgcgttggccgattcattaatgcagctg gcacgacaggtttcccgactggaaagcgggcagtgagcgcaacgcaattaatgtgagt tagctcactcattaggcaccccaggctttacactttatgcttccggctcgtatgttgt gtggaattgtgagcggataacaatttcacacaggaaacagctatgaccatgattacgc caagcgcgcaattaaccctcactaaagggaacaaaagctgggtaccgggccccccctc gaggtcgacggtatcgataagcttgatatc
``` attH4X:
SEQ ID NO: 31
```
acgctttatttcattaagttg
```

Example 1: Rapid E. coli Chromosomal Integration

The present example follows the methodology depicted in FIG. 2. C3INT-HIS-PET22b(+) was amplified with petF2 (SEQ ID NO: 10) and petR (SEQ ID NO: 11) and the PCR product subsequently intramolecularly ligated to produce a C3INT-HIS minicircle. attP-PET22b(+) was amplified with attP-F (SEQ ID NO: 12) and attPSOE-R (SEQ ID NO: 13) while PET22b(+) was amplified with TEM1prom-F (SEQ ID NO: 14) and TEM1promR (SEQ ID NO: 15) which produced PCR products encoding attP and ampicillin-resistant gene respectively. Splice overlap extension PCR (SOE-PCR) was carried out with these two PCR products using attP-F (SEQ ID NO: 12) and TEM1prom-R (SEQ ID NO: 15). The PCR product was subsequently intramolecularly ligated to produce attP-TEM1 minicircle. 100 ng of C3INT-HIS minicircle and 100 ng attP-TEM1 minicircle were combined and electroporated to 25 μL electrocompetent TG1 cells. The cells were allowed to recover for 1 hr before being plated on varying concentrations of ampicillin-LB agar plates (0.01 mg/mL, 0.02 mg/mL, 0.05 mg/mL, 0.07 mg/mL and 0.1 mg/mL). Incubation was carried out at 37° C. for 12-14 hrs to allow for expression of C3 integrase and chromosomal integration of the ampicillin-resistance cassette by C3 integrase. Colony PCR was carried out with EcoliAttB-F (SEQ ID NO: 16) and EcoliAttB-R (SEQ ID NO: TEM1prom-F (SEQ ID NO: 14) and EcoliAttB-F (SEQ ID NO: 16), or TEM1prom-F (SEQ ID NO: 14) and Ecoli-AttB-R (SEQ ID NO: 17) to verify the presence of chromosomal integration of the ampicillin-resistance cassette. The PCR products were also sequenced with the same primers to confirm the results. The sequencing indicated a correct integration event into the chromosomal attB site (FIG. 3C).

Example 2 Recombination Activity of the Parental and Integrase Variants C2 and C3

Figure 4A:
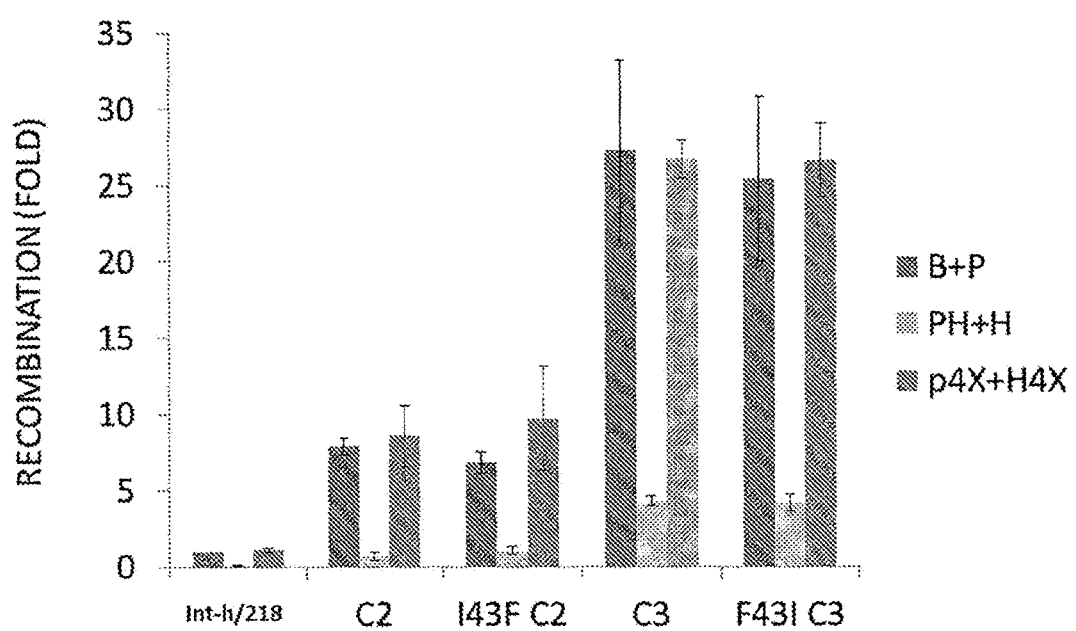
FIG. 4A shows the improved intramolecular recombination activity of parental Int-h/218 and indicated lambda integrase mutants expressed using an in vitro transcription/translation system for cognate (attB/attP) and non-cognate (attH/attPH and attH4x/attP4x) sites. Recombination is denoted relative to parental Int-h/218 efficiency with attB/P substrate (set to 1). Mutant lambda integrase proteins of the invention (C2 and C3) are more efficient at performing the respective recombination reactions. C2 denotes lambda integrase mutants with the D336V mutation. I43F C2 denotes the C2 lambda integrase mutants with an additional I43F mutation. C3 denotes lambda integrase mutants with the I43F, E319G, D336V mutations. N=2, bars indicate means +/− SD.

The present example demonstrates the recombination activity of the parental Int-h/218 and selected mutants (C2, C3 and indicated variants thereof). FIG. 4A depicts results from an in vitro intramolecular recombination reaction using integrases produced by in vitro transcription/translation. Plasmids encoding the respective integrase (Int-h/218, C2, C3 or variant thereof) were amplified using primers IntRBS-F and INTstop-R, and the PCR products re-amplified with primers. Univeral and INTstop-R to get integrase amplicons with T7 promoter and ribosame binding site requited for in vitro transcription-translation (IVT). 20 ng of each integrase amplicon was expressed using PURExpress® In Vitro Protein Synthesis Kit in a total volume of 9 μL at 30° C. for 1 hour. Intramolecular recombination was then carried out by adding 10 ng plasmid substrate containing either attB/attP sites, attPH/attH sites or attH4x/attP4x sites (FIG. 1) to a total volume of 10 μL. The mixture was allowed to incubate for 2 hours at 37° C. The reaction was Subsequently diluted 1/10 before taking 1 μL for real-time PCR quantification of recombination efficiency. Real-time PCR quantification was carried out with 250 nm each of primers pLIR-F1 (SEQ ID No: 27) and pLIR-R1 (SEQ ID NO: 28) in a final volume of 20 μL with SsoAdvanced™ Universal® SYBRO® Green Supermix. The activities of the recombinant integrase proteins are presented relative to activity of WT Int-h/218 on attB/attP plasmid substrate (set as value of 1). Error bars indicate standard deviation of two independent experiments.

The results show significant increases in recombination efficiency for the C2 and C3 integrases compared to parental Int-h/218. The data in FIG. 4 show the strong contribution of the E319G mutation present in C3 on the efficiency of intramolecular recombination. Removing this mutation from C3 yields I43F C2 which shows fold reduced activity on all substrate pairs tested. The contribution of the I43F mutation for intramolecular recombination is not readily apparent, as addition of this to C2 or removal from C3 does not lead to any significant. Change in recombination efficiency. However, it could impact on other parameters such as intermolecular recombination in vivo and/or protein stability.

Figure 4B:
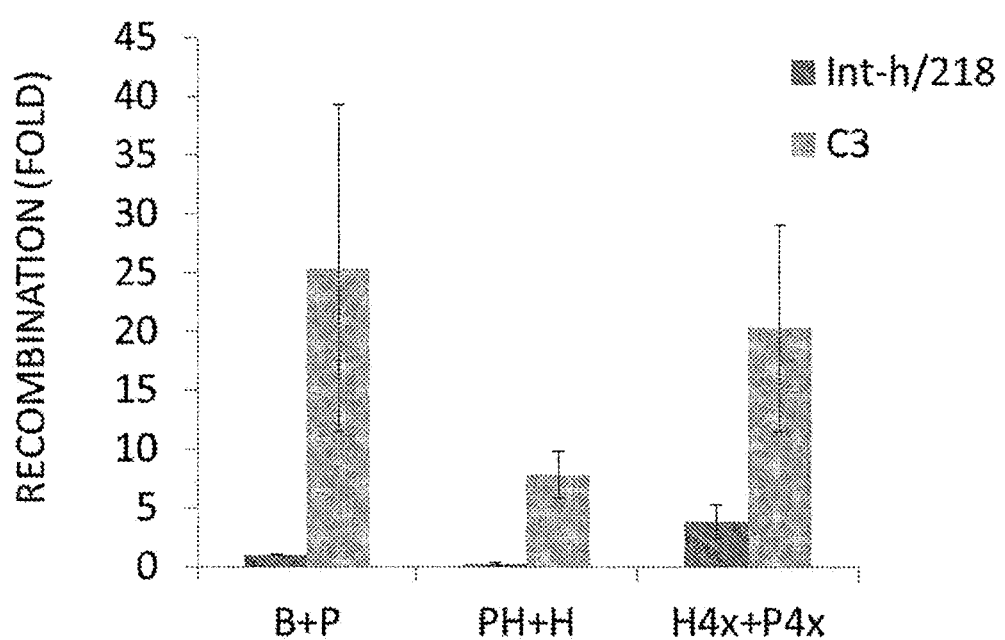
FIG. 4B shows intramolecular recombination activity of parental Int-h/218 and C3 integrase on indicated substrates. Intramolecular recombination was carried out with 5 µg of purified recombinant integrase protein incubated with 10 ng plasmid substrate containing either attB/attP sites, attH/attPH sites or attH4x/attP4x sites. The reaction volume was 25 µL and was carried out for 1.5 hours at 37° C. in recombination buffer (100 mM Tris pH 7.5, 500 mM NaCl, 25 mM DTT, 10 mM EDTA, 5 mg/mL bovine serum albumin). The reaction was diluted 1/10 before taking 2 µL for real-time PCR quantification of recombination efficiency. Real-time PCR quantification was carried out with 250 nM each of primers pLIR-F1 (SEQ ID NO: 27) and pLIR-R1 (SEQ ID NO: 28) in a final volume of 20 µL with SsoAdvanced™ Universal SYBR® Green Supermix. The activities of the recombinant integrase proteins are presented relative to activity of Int-h/218 on attB/attP plasmid substrate (set as value of 1). Error bars indicate average +/− SD of 2 independent experiments.

FIG. 4B depicts results from in an vitro intramolecular recombination reaction using integrases produced recombinantly in E. coli. Plasmids expressing integrase Int-h/218 and C3 were transformed into E. coli BL21(DE3)pLysS (Invitrogen) competent cells. The bacterial cells were grown in LB medium at 37° C. and induced at $OD_{600\ nm}$ of ~0.6 with 0.5 mM IPTG at 30° C. for 6 hours. The cells were then harvested by centrifugation, resuspended in 50 mM Tris pH 8.0, 1M NaCl, 20 mM Imidazole and lysed by sonication. The cell lysate was clarified by high-speed centrifugation and the supernatant was then applied to a 1 mL HisTrap™ FF column (GE Healthcare) pre-equilibrated in binding buffer of 50 mM Tris-HCl pH 8.0, 1M NaCl, 20 mM Imidazole, 0.5 mM EDTA and 2 mM DTT. The column was washed with binding buffer and the integrase proteins were eluted off the column with 50 mM Tris-HCl pH 8.0, 1M NaCl, 500 mM Imidazole, 0.5 mM EDTA and 2 mM DTT. Collected fractions were analyzed by SDS-PAGE gel and the appropriate fractions were dialyzed and concentrated in 50 mM Tris pH 8.0, 1M NaCl, 0.5 mM EDTA and 2 mM DTT using Amicon-Ultra (10 kDa MWCO) prior to storage at −80° C.

Intramolecular recombination was carried out with 5 µg of purified recombinant integrase protein incubated with 10 ng plasmid substrate containing either attB/attP sites, attPH/attH sites or attH4x/attP4x sites. The reaction volume was 25 µL and was carried out for 1.5 hours at 37° C. in recombination buffer (100 mM Tris pH 7.5, 500 mM NaCl, 25 mM DTT, 10 mM EDTA, 5 mg/mL bovine serum albumin). The reaction was diluted 1/10 before taking 2 µL for real-time PCR quantification of recombination efficiency. Real-time PCR quantification was carried out with 250 nM each of primers pLIR-F1 (SEQ ID NO: 27) and pLIR-R1 (SEQ ID NO: 28) in a final volume of 20 µL with SsoAdvanced™ Universal SYBR® Green Supermix. The activities of the recombinant integrase proteins are presented relative to activity of Int-h/218 (WT) on attB/attP plasmid substrate (set as value of 1). Error bars indicate average +/− SD of 2 independent experiments. The data again show increased recombination on all substrates tested for the C3 integrase compared to Int-h/218 parent.

The improved recombination activities of C2 and C3 observed in these experiments (FIGS. 4A and 4B) correlate with those seen in cell-based assays (FIG. 5)

Example 3: Cell Culture Conditions, Transfection Procedure and Selection of Puromycin-Resistant Recombinants for Endogenous attH4x Targeting in HT1080 Cells For endogenous targeting in the HT1080 cell line, 3×10$^6$ cells were seeded in Dulbecco's Modified Eagle Medium [DMEM (Life technologies) supplemented with 10% FBS, 1% L-glutamine and 100 units/mL of Penicillin and Streptomycin each per 10 cm cell culture dish a day before transfection to obtain 70-90% confluence at the time of transfection. Transfections were done using Lipofectamine 2000 reagent (Life technologies). Plasmid DNA-Lipid complexes were prepared by mixing 5 ng of the targeting vector (pPGKssPuro-attP4x (SEQ ID NO: 29)) and 100 ng of the integrase expression plasmid (pCMVsSK2-IntC3-CNLS (SEQ ID NO: 30)) diluted in 75 µl of Opti-MEM medium with 2.5 µl of Lipofectamine 2000 reagent diluted in 75 µL of Opti-MEM medium (Life technologies) and incubating for 20 minutes at room temperature. The transfection mix was added onto the cells (under DMEM without antibiotics) and transfection was allowed to proceed for 4-6 hours following which the complexes were removed by replacing with fresh medium. 48 hours post-transfection, the cells were grown in growth medium containing 3 µg Puromycin per ml to select for puromycin-resistant colonies. After 3 weeks of selection, puromycin-resistant colonies were picked and expanded. Genomic DNA was extracted using DNeasy Blood & Tissue Kit (Qiagen).

Example 4: Cell Culture Conditions, Transfection Procedure and FACS Analysis for Episomal Intra-Molecular Recombination Assay For the episomal intra-molecular recombination assays in HT1080 cell line, 3×10$^5$ cells were seeded in Dulbecco's Modified Eagle Medium [DMEM (Life technologies) supplemented with 10% FBS, 1% L-glutamine and 100 Units/mL of Penicillin and Streptomycin each) per well of 6 well plate a day before transfection to obtain 70-90% confluence at the time of transfection. Transfections were done using Lipofectamine 2000 reagent. For every transfection per well, plasmid DNA-Lipid complexes were prepared by mixing 1.5 µg of pLIR and 1.5 µg of the A integrate expression plasmid diluted in 100 µl of Opti-MEM medium with 6 µl of Lipofectamine 2000 reagent diluted in 100 µl of Opti-MEM medium and incubating for 20 minutes at room temperature. The transfection mix was added dropwise onto the cells (under DMEM without antibiotics) and transfection was allowed to proceed for 4-6 hours following which the complexes were removed by replacing with fresh DMEM medium. 48-72 hours post-transfection, the cells were trypsinised and harvested with DMEM into eppendorf tubes, pelleted by centrifugation (at 1000× ref for 5 minutes) and resuspended in 1 ml fresh DMEM. GFP positive cell were quantified by FACS on a BD FACSCalibur™ machine (Becton-Dickinson).

Example 5: Identifying Successful Sequence Specific Recombination Event

PGR was performed using GoTaq Flexi DNA polymerase (Promega) with primers HOP' attH4X_F1 (SEQ ID NO: 25) and PuroRev24 (SEQ ID NO: 26) and 200 ng of genomic DNA as template per PCR reaction in 50 µl volume. The following thermal cycling parameters were used for the PCR: an initial step of 95° C. for 5 minutes, 35 cycles of 95° C. for 1 minute, 57° C. for 30 seconds and 72° C. for 1 minute, and a final step of 72° C. for 5 minutes. The PCR samples were analyzed by electrophoresis in 0.8% agarose gel in Tris-Boric acid-EDTA buffer.

Figure 6A:
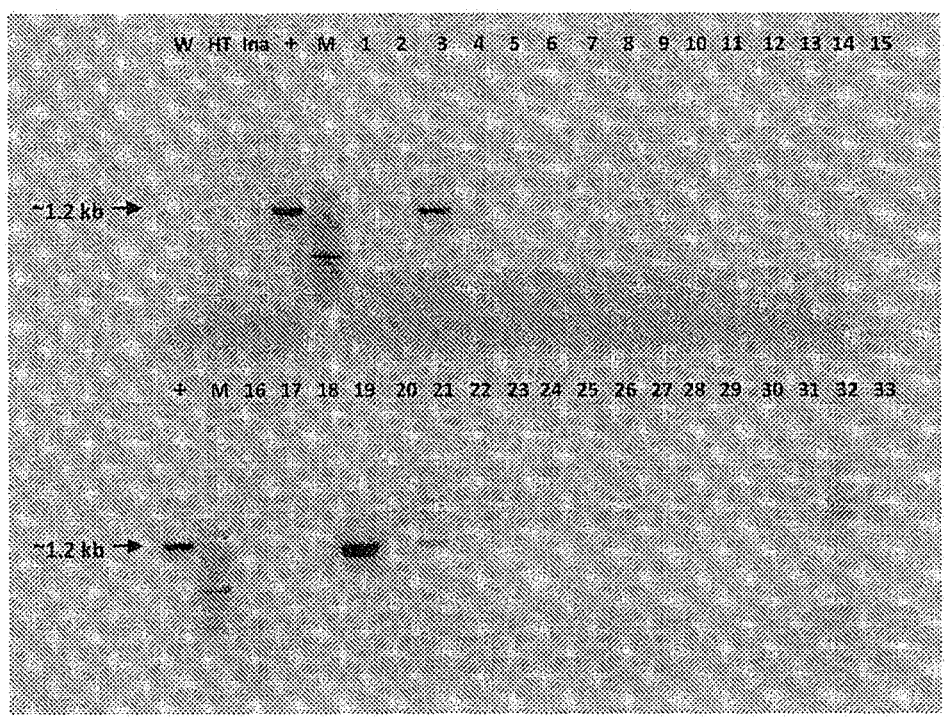
FIG. 6A shows the PCR results, of screening for attH4x and attP4x recombination events at L1 loci in the HT1080 clones. PCR amplifications of the expected size (~1200 bp; for the attL site generated through recombination between attH4x and attP4x) were detected for the HT1080 clones 3, 19 and 21. W, no DNA template control; HT, negative control (genomic DNA from the parental HT1080 cells); Ina, genomic DNA from puromycin resistant colonies obtained through co-transfection of pPGKssPuro-attP4x and pCMVssKZ-Inactivie Int (plasmid expressing integrase with an inactivating mutation wherein the amino acid residue tyrosine at sequence position 342 is replaced by the amino acid alanine); +, positive control (genomic DNA from HT1080 clone having an attH4x X attP4x integration event in L1 element); M, 100 bp DNA ladder; 1 to 33, genomic DNA from puromycin resistant HT1080 colonies obtained through co-transfection of pPGKssPuro-attP4'x and pCMVssKZ-IntC3-CNLS.

FIG. 6A depicts the PCR results of screening for attH4x and attP4x recombination events at the L1 loci in the HT1080 clones. PCR amplifications of the expected size (~1200 bp; for the attL site generated through recombination between attH4x and attP4x) were detected for the HT1080 clones 3, 19 and 21. FIG. 6B shows the nucleotide sequence of attL site generated through recombination between the attH4x and attP4x in the HT1080 clones 3 and 19.

APPLICATIONS

The improved in vitro recombination by using the integrase variants of the present invention and the attH/attPH and atth4X/attP4X substrate pairs indicates that the integrase variants described herein may be a useful reagent, tool for biotechnology applications such as recombination-based cloning applications.

It will be apparent that various other modifications and adaptations of the invention will be apparent to the person skilled in the art after reading the foregoing disclosure without departing from the spirit and scope of the invention and it is intended that all such modifications and adaptations dome within the scope of the appended claims.

What is claimed is:

1. A lambda integrase mutant comprising the amino acid sequence of SEQ ID NO: 1, except for an amino acid mutations at a position corresponding to residues 336 of the amino acid sequence of SEQ ID NO: 1, wherein the aspartate corresponding to position 336 of SEQ ID NO: 1 is replaced by a hydrophobic amino acid, and wherein the lambda integrase mutant has integrase activity.

2. The lambda integrase mutant according to claim 1, wherein the aspartate corresponding to position 336 of SEQ ID NO: 1 is replaced by a hydrophobic amino acid selected from the group consisting of isoleucine, leucine and valine.

3. The lambda integrase mutant according to claim 1, wherein the aspartate corresponding to position 336 of SEQ ID NO: 1 is replaced by valine.

4. A nucleic acid molecule comprising a nucleotide sequence encoding the lambda integrase mutant of claim 1.

5. The nucleic acid molecule according to claim 4, wherein the nucleic acid molecule is operably linked to a regulatory sequence to permit expression of the nucleic acid molecule, optionally wherein the regulatory sequence comprises a promoter sequence, and optionally wherein the nucleic acid molecule is located in a vector.

6. An isolated host cell comprising the nucleic acid molecule according to claim 4.

7. A method of recombining a nucleic acid of interest into a target nucleic acid, the method comprising contacting a targeting nucleic acid comprising the nucleic acid of interest with the target nucleic acid in the presence of a lambda integrase mutant to thereby recombine the nucleic acid of interest into the target nucleic acid, wherein the lambda integrase mutant comprises the amino acid sequence of SEQ ID NO: 1, except for an amino acid mutations at a position corresponding to residue 336 of the amino acid sequence of SEQ ID NO: 1, wherein the aspartate corresponding to position 336 of SEQ ID NO: 1 is replaced by a hydrophobic amino acid, and wherein the lambda integrase mutant has integrase activity.

8. The method according to claim 7, wherein the target nucleic acid comprises DNA, optionally wherein the target nucleic acid comprises genomic DNA, optionally wherein the target nucleic acid comprises a sequence selected from the group consisting of an attH sequence comprising the nucleotide sequence of SEQ ID NO: 7 and an attH4X sequence comprising the nucleotide sequence of SEQ ID NO: 31, optionally wherein the targeting nucleic acid is a vector, optionally wherein the targeting nucleic acid comprises a sequence selected from the group consisting of an attPH sequence comprising the nucleotide sequence of SEQ ID NO: 8 and an attP4X sequence comprising the nucleotide sequence of SEQ ID NO: 9.

9. The method according to claim 7, wherein the recombination is performed in the presence of one or more cofactors, optionally wherein the one or more cofactors is selected from the group consisting of excisionase (XIS), factor for inversion simulation (FIS) and integration host factor (IHF).

10. The method according to claim 8, wherein the genomic DNA is comprised in an isolated cell.

11. A sequence specific recombination kit comprising:
   a. a targeting nucleic acid into which a nucleic acid of interest can be inserted, and
   b. the lambda integrase mutant of claim 1, or a nucleic acid molecule comprising a nucleotide sequence encoding the lambda integrase mutant of claim 1.

12. The kit according to claim 11, further comprising at least one reagent for inserting said nucleic acid of interest into said targeting nucleic acid, optionally wherein said targeting nucleic acid comprises a sequence selected from the group consisting of an attPH sequence comprising the nucleotide sequence of SEQ ID NO: 8 and an attP4X sequence comprising the nucleotide sequence of SEQ ID NO: 9, optionally wherein said targeting nucleic acid comprises a sequence selected from the group consisting of an attH sequence comprising the nucleotide sequence of SEQ ID NO: 7 and an attH4X sequence comprising the nucleotide sequence of SEQ ID NO: 31.

13. The kit according to claim 11, further comprising buffer(s) and/or instructions for recombining said nucleic acid of interest with a given target nucleic acid, optionally further comprising at least one reagent for determining a successful sequence specific recombination event, optionally wherein said reagent is a primer pair.

* * * * *

SEQUENCE LISTING

<160> NUMBER OF SEQ ID NOS: 34

<210> SEQ ID NO 1
<211> LENGTH: 356
<212> TYPE: PRT
<213> ORGANISM: Bacteriophage lambda

<400> SEQUENCE: 1

```
Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240
```

Ala Ile Pro Thr Ala Leu His Ile Asp Ala Leu Gly Ile Ser Met Lys
            245                 250                 255

Glu Thr Leu Asp Lys Cys Lys Glu Ile Leu Gly Gly Glu Thr Ile Ile
        260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
            355

<210> SEQ ID NO 2
<211> LENGTH: 356
<212> TYPE: PRT
<213> ORGANISM: Artificial Sequence
<220> FEATURE:
<223> OTHER INFORMATION: C2 lambda integrase mutant

<400> SEQUENCE: 2

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
            245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
            275                 280                 285

Phe Met Arg Ala Arg Lys Ala Ser Gly Leu Ser Phe Glu Gly Asp Pro
290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Val
                325                 330                 335

Thr Met Ala Ser Gln Tyr Arg Asp Asp Arg Gly Arg Glu Trp Asp Lys
            340                 345                 350

Ile Glu Ile Lys
            355

<210> SEQ ID NO 3
<211> LENGTH: 356
<212> TYPE: PRT
<213> ORGANISM: Artificial Sequence
<220> FEATURE:
<223> OTHER INFORMATION: C3 lambda integrase mutant

<400> SEQUENCE: 3

Met Gly Arg Arg Ser His Glu Arg Asp Leu Pro Pro Asn Leu
1               5                   10                  15

Tyr Ile Arg Asn Asn Gly Tyr Tyr Cys Tyr Arg Asp Pro Arg Thr Gly
                20                  25                  30

Lys Glu Phe Gly Leu Gly Arg Asp Arg Arg Phe Ala Ile Thr Glu Ala
            35                  40                  45

Ile Gln Ala Asn Ile Glu Leu Phe Ser Gly His Lys His Lys Pro Leu
        50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240

```
Ala Ile Pro Thr Ala Leu His Ile Asp Ala Leu Gly Ile Ser Met Lys
            245                 250                 255

Glu Thr Leu Asp Lys Cys Lys Glu Ile Leu Gly Gly Glu Thr Ile Ile
        260                 265                 270

Ala Ser Thr Arg Arg Glu Pro Leu Ser Ser Gly Thr Val Ser Arg Tyr
    275                 280                 285

Phe Met Arg Ala Arg Lys Ala Ser Gly Leu Ser Phe Glu Gly Asp Pro
290                 295                 300

Pro Thr Phe His Glu Leu Arg Ser Leu Ser Ala Arg Leu Tyr Gly Lys
305                 310                 315                 320

Gln Ile Ser Asp Lys Phe Ala Gln His Leu Leu Gly His Lys Ser Val
                325                 330                 335

Thr Met Ala Ser Gln Tyr Arg Asp Asp Arg Gly Arg Glu Trp Asp Lys
            340                 345                 350

Ile Glu Ile Lys
        355

<210> SEQ ID NO 4
<211> LENGTH: 1071
<212> TYPE: DNA
<213> ORGANISM: Bacteriophage lambda

<400> SEQUENCE: 4
atgggaagaa ggcgaagtca tgagcgccgg gatttacccc ctaacctta tataagaaac      60 aatggatatt actgctacag ggacccaagg acgggtaaag agtttggatt aggcagagac    120
aggcgaatcg caatcactga agctatacag gccaacattg agttattttc aggacacaaa    180
cacaagcctc tgacagcgag aatcaacagt gataattccg ttacgttaca ttcatggctt    240
gatcgctacg aaaaaatcct ggccagcaga ggaatcaagc agaagacact cataaattac    300
atgagcaaaa ttaaagcaat aaggaggggt ctgcctgatg ctccacttga agacatcacc    360
acaaaagaaa ttgcggcaat gctcaatgga tacatagacg agggcaaggc ggcgtcagcc    420
aagttaatca gatcaacact gagcgatgca ttccgagagg caatagctga aggccatata    480
acaacaaacc atgtcgctgc cactcgcgca gcaaaatcaa aggtaaggag atcaagactt    540
acggctgacg aatacctgaa aatttatcaa gcagcagaat catcaccatg ttggctcaga    600
cttgcaatgg aactggctgt tgttaccggg caacgagttg tgatttatg caaaatgaag    660 tggtctgata tcgtagatgg atatctttat gtcgagcaaa gcaaaacagg cgtaaaaatt    720
gccatcccaa cagcattgca tattgatgct ctcggaatat caatgaagga aacacttgat    780
aaatgcaaag agattcttgg cggagaaacc ataattgcat ctactcgtcg cgaaccgctt    840
tcatccggca cagtatcaag gtattttatg cgcgcacgaa aagcatcagg tctttccttc    900
gaaggggatc cgcctacctt tcacgagttg cgcagtttgt ctgcaagact ctatgagaag    960
cagataagcg ataagtttgc tcaacatctt ctcgggcata agtcggacac catggcatca   1020
cagtatcgtg atgacagagg cagggagtgg gacaaaattg aaatcaaata a            1071

<210> SEQ ID NO 5
<211> LENGTH: 21
<212> TYPE: DNA
<213> ORGANISM: Artificial Sequence
<220> FEATURE:
<223> OTHER INFORMATION: attB attachment site

<400> SEQUENCE: 5
```

-continued ctgcttttttt atactaactt g 21

<210> SEQ ID NO 6
<211> LENGTH: 21
<212> TYPE: DNA
<213> ORGANISM: Artificial Sequence
<220> FEATURE:
<223> OTHER INFORMATION: attP attachment site

<400> SEQUENCE: 6 cagcttttttt atactaagtt g 21

<210> SEQ ID NO 7
<211> LENGTH: 21
<212> TYPE: DNA
<213> ORGANISM: Artificial Sequence
<220> FEATURE:
<223> OTHER INFORMATION: attH attachment site

<400> SEQUENCE: 7
ctgctttctt ataccaagtg g 21

<210> SEQ ID NO 8
<211> LENGTH: 21
<212> TYPE: DNA
<213> ORGANISM: Artificial Sequence
<220> FEATURE:
<223> OTHER INFORMATION: attPH attachment site

<400> SEQUENCE: 8
cagctttctt ataccaagtg g 21

<210> SEQ ID NO 9
<211> LENGTH: 21
<212> TYPE: DNA
<213> ORGANISM: Artificial Sequence
<220> FEATURE:
<223> OTHER INFORMATION: attP4X attachment site

<400> SEQUENCE: 9
cagctttatt tcattaagtt g 21

<210> SEQ ID NO 10
<211> LENGTH: 19
<212> TYPE: DNA
<213> ORGANISM: Artificial Sequence
<220> FEATURE:
<223> OTHER INFORMATION: petF2 Primer

<400> SEQUENCE: 10
catcggtgat gtcggcgat 19

<210> SEQ ID NO 11
<211> LENGTH: 24
<212> TYPE: DNA
<213> ORGANISM: Artificial Sequence
<220> FEATURE:
<223> OTHER INFORMATION: petR Primer

<400> SEQUENCE: 11
cggatatagt tcctcctttc agca 24

<210> SEQ ID NO 12
<211> LENGTH: 38
<212> TYPE: DNA
<213> ORGANISM: Artificial Sequence

```
<220> FEATURE:
<223> OTHER INFORMATION: attP-F Primer

<400> SEQUENCE: 12
cacagaattc cgtctgttac aggtcactaa taccatct                                  38

<210> SEQ ID NO 13
<211> LENGTH: 52
<212> TYPE: DNA
<213> ORGANISM: Artificial Sequence
<220> FEATURE:
<223> OTHER INFORMATION: attPSOE-R Primer

<400> SEQUENCE: 13
acatttcccc gaaaagtgcc acctgaacat caccgggaaa tcaaataatg at                  52

<210> SEQ ID NO 14
<211> LENGTH: 27
<212> TYPE: DNA
<213> ORGANISM: Artificial Sequence
<220> FEATURE:
<223> OTHER INFORMATION: TEM1prom-F Primer

<400> SEQUENCE: 14
ttcaggtggc actttcgg gaaatgt                                                27

<210> SEQ ID NO 15
<211> LENGTH: 41
<212> TYPE: DNA
<213> ORGANISM: Artificial Sequence
<220> FEATURE:
<223> OTHER INFORMATION: TEM1prom-R Primer

<400> SEQUENCE: 15
tgtggaattc ctacactaga aggacagtat ttggtatctg c                              41

<210> SEQ ID NO 16
<211> LENGTH: 24
<212> TYPE: DNA
<213> ORGANISM: Artificial Sequence
<220> FEATURE:
<223> OTHER INFORMATION: EcoliAttB-F Primer

<400> SEQUENCE: 16
ctgaaaatgt gttcacaggt tgct                                                 24

<210> SEQ ID NO 17
<211> LENGTH: 21
<212> TYPE: DNA
<213> ORGANISM: Artificial Sequence
<220> FEATURE:
<223> OTHER INFORMATION: EcoliattB-R Primer

<400> SEQUENCE: 17
gcaatgccat ctggtatcac t                                                    21

<210> SEQ ID NO 18
<211> LENGTH: 1071
<212> TYPE: DNA
<213> ORGANISM: Artificial Sequence
<220> FEATURE:
<223> OTHER INFORMATION: C2 mutant gene

<400> SEQUENCE: 18
atgggaagaa ggcgaagtca tgagcgccgg gatttacccc ctaacctta tataagaaac           60
```

| | |
|---|---|
| aatggatatt actgctacag ggacccaagg acgggtaaag agtttggatt aggcagagac | 120 |
| aggcgaatcg caatcactga agctatacag gccaacattg agttattttc aggacacaaa | 180 |
| cacaagcctc tgacagcgag aatcaacagt gataattccg ttacgttaca ttcatggctt | 240 |
| gatcgctacg aaaaaatcct ggccagcaga ggaatcaagc agaagacact cataaattac | 300 |
| atgagcaaaa ttaaagcaat aaggaggggt ctgcctgatg ctccacttga agacatcacc | 360 |
| acaaaagaaa ttgcggcaat gctcaatgga tacatagacg agggcaaggc ggcgtcagcc | 420 |
| aagttaatca gatcaacgct gagcgatgca ttccgagagg caatagctga aggccatata | 480 |
| acaacaaacc atgtcgctgc cactcgcgca gcaaagtcaa aggtaaggag atcaagactt | 540 |
| acggctgacg aatacctgaa aatttatcaa gcagcagaat catcaccatg ttggctcaga | 600 |
| cttgcaatgg aactggctgt tgttaccggg caacgagttg gtgacttgtg caaaatgaag | 660 |
| tggtctgata tcgtagatgg atatctttat gtcgagcaaa gcaaaacagg cgtaaaaatt | 720 |
| gccatcccaa cagcattgca tattgatgct ctcggaatat caatgaagga aacacttgat | 780 |
| aaaatgcaaag agattcttgg cggagaaacc ataattgcat ctactcgtcg cgaaccgctt | 840 |
| tcatccggca cagtatcaag gtattttatg cgcgcacgaa aagcatcagg tctttccttc | 900 |
| gaaggggatc cgcctacctt tcacgagttg cgcagtttgt ctgcaagact ctatgagaag | 960 |
| cagataagcg ataagtttgc tcaacatctt ctcgggcata agtcggtcac catggcatca | 1020 |
| cagtatcgtg atgacagagg cagggagtgg gacaaaattg aaatcaaata a | 1071 |

<210> SEQ ID NO 19
<211> LENGTH: 1071
<212> TYPE: DNA
<213> ORGANISM: Artificial Sequence
<220> FEATURE:
<223> OTHER INFORMATION: C3 mutant gene

<400> SEQUENCE: 19

| | |
|---|---|
| atgggaagaa ggcgaagtca tgagcgccgg gatttacccc ctaacctttta tataagaaac | 60 |
| aatggatatt actgctacag ggacccaagg acgggtaaag agtttggatt aggcagagac | 120 |
| aggcgattcg caatcactga agctatacag gccaacattg agttattttc aggacacaaa | 180 |
| cacaagcctc tgacagcgag aatcaacagt gataattccg ttacgttaca ttcatggctt | 240 |
| gatcgctacg aaaaaatcct ggccagcaga ggaatcaagc agaagacact cataaattac | 300 |
| atgagcaaaa ttaaagcaat aaggaggggt ctgcctgatg ctccacttga agacatcacc | 360 |
| acaaaagaaa ttgcggcaat gctcaatgga tacatagacg agggcaaggc ggcgtcagcc | 420 |
| aagttaatca gatcaacgct gagcgatgca ttccgagagg caatagctga aggccatata | 480 |
| acaacaaacc atgtcgctgc cactcgcgcg gcaaagtcaa aggtaaggag atcaagactt | 540 |
| acggctgacg aatacctgaa aatttatcaa gcagcagaat catcaccatg ttggctcaga | 600 |
| cttgcaatgg aactggctgt tgttaccggg caacgagttg gtgacttgtg caaaatgaag | 660 |
| tggtctgata tcgtagatgg atatctttat gtcgagcaaa gcaaaacagg cgtaaaaatt | 720 |
| gccatcccaa cagcattgca tattgatgct ctcggaatat caatgaagga aacacttgat | 780 |
| aaaatgcaaag agattcttgg cggagaaacc ataattgcat ctactcgtcg cgaaccgctc | 840 |
| tcatccggca cagtatcaag gtattttatg cgcgcacgaa aagcatcagg tctttccttc | 900 |
| gaaggggatc cgcctacctt tcacgagttg cgcagtttgt ctgcaagact ctatgggaag | 960 |
| cagataagcg ataagtttgc tcaacatctt ctcgggcata agtcggtcac catggcatca | 1020 |
| cagtatcgtg atgacagagg cagggagtgg gacaaaattg aaatcaaata a | 1071 |

<210> SEQ ID NO 20
<211> LENGTH: 1481
<212> TYPE: DNA
<213> ORGANISM: Artificial Sequence
<220> FEATURE:
<223> OTHER INFORMATION: C3 mutant minicircle DNA

<400> SEQUENCE: 20

| | | | | | |
|---|---|---|---|---|---|
| catcggtgat | gtcggcgata | taggcgccag | caaccgcacc | tgtggcgccg | gtgatgccgg | 60 |
| ccacgatgcg | tccggcgtag | aggatcgaga | tctcgatccc | gcgaaattaa | tacgactcac | 120 |
| tatagggaa | ttgtgagcgg | ataacaattc | ccctctagaa | ataattttgt | ttaactttaa | 180 |
| gaaggagata | tacatatggg | aagaaggcga | agtcatgagc | gccgggattt | accccctaac | 240 |
| ctttatataa | gaaacaatgg | atattactgc | tacaggacc | caaggacggg | taaagagttt | 300 |
| ggattaggca | gagacaggcg | attcgcaatc | actgaagcta | tacaggccaa | cattgagtta | 360 |
| ttttcaggac | acaaacacaa | gcctctgaca | gcgagaatca | acagtgataa | ttccgttacg | 420 |
| ttacattcat | ggcttgatcg | ctacgaaaaa | atcctggcca | gcagaggaat | caagcagaag | 480 |
| acactcataa | attacatgag | caaaattaaa | gcaataagga | ggggtctgcc | tgatgctcca | 540 |
| cttgaagaca | tcaccacaaa | agaaattgcg | gcaatgctca | atggatacat | agacgagggc | 600 |
| aaggcggcgt | cagccaagtt | aatcagatca | acgctgagcg | atgcattccg | agaggcaata | 660 |
| gctgaaggcc | atataacaac | aaaccatgtc | gctgccactc | gcgcggcaaa | gtcaaaggta | 720 |
| aggagatcaa | gacttacggc | tgacgaatac | ctgaaaattt | atcaagcagc | agaatcatca | 780 |
| ccatgttggc | tcagacttgc | aatggaactg | gctgttgtta | ccgggcaacg | agttggtgac | 840 |
| ttgtgcaaaa | tgaagtggtc | tgatatcgta | gatggatatc | tttatgtcga | gcaaagcaaa | 900 |
| acaggcgtaa | aaattgccat | cccaacagca | ttgcatattg | atgctctcgg | aatatcaatg | 960 |
| aaggaaacac | ttgataaatg | caaagagatt | cttggcggag | aaaccataat | tgcatctact | 1020 |
| cgtcgcgaac | cgctctcatc | cggcacagta | tcaaggtatt | tatgcgcgc | acgaaaagca | 1080 |
| tcaggtcttt | ccttcgaagg | ggatccgcct | acctttcacg | agttgcgcag | tttgtctgca | 1140 |
| agactctatg | ggaagcagat | aagcgataag | tttgctcaac | atcttctcgg | gcataagtcg | 1200 |
| gtcaccatgg | catcacagta | tcgtgatgac | agaggcaggg | agtgggacaa | aattgaaatc | 1260 |
| aaacatcatc | accatcacca | ctaatgaaa | ttcgagctcc | gtcgacaagc | ttgcggccgc | 1320 |
| actcgagcac | caccaccacc | accactgaga | tccggctgct | aacaaagccc | gaaaggaagc | 1380 |
| tgagttggct | gctgccaccg | ctgagcaata | actagcataa | ccccttgggg | cctctaaacg | 1440 |
| ggtcttgagg | ggttttttgc | tgaaaggagg | aactatatcc | g | | 1481 |

<210> SEQ ID NO 21
<211> LENGTH: 1599
<212> TYPE: DNA
<213> ORGANISM: Artificial Sequence
<220> FEATURE:
<223> OTHER INFORMATION: attP-TEM1 minicircle

<400> SEQUENCE: 21

| | | | | | |
|---|---|---|---|---|---|
| cacagaattc | cgtctgttac | aggtcactaa | taccatctaa | gtagttgatt | catagtgact | 60 |
| gcatatattg | tgttttacag | tattatgtag | tctgtttttt | atgcaaaatc | taatttaata | 120 |
| tattgatatt | tatatcattt | tacgtttctc | gttcagcttt | tttatactaa | gttggcatta | 180 |
| taaaaagca | ttgcttatca | atttgttgca | acgaacaggt | cactatcagt | caaaataaaa | 240 |

```
tcattatttg atttcccggt gatgttcagg tggcactttt cggggaaatg tgcgcggaac      300
ccctatttgt ttatttttct aaatacattc aaatatgtat ccgctcatga gacaataacc      360
ctgataaatg cttcaataat attgaaaaag gaagagtatg agtattcaac atttccgtgt      420
cgcccttatt ccctttttg cggcattttg ccttcctgtt tttgctcacc cagaaacgct       480
ggtgaaagta aaagatgctg aagatcagtt gggtgcacga gtgggttaca tcgaactgga      540
tctcaacagc ggtaagatcc ttgagagttt tcgccccgaa gaacgttttc caatgatgag      600
cacttttaaa gttctgctat gtggcgcggt attatcccgt attgacgccg ggcaagagca      660
actcggtcgc cgcatacact attctcagaa tgacttggtt gagtactcac cagtcacaga      720
aaagcatctt acggatggca tgacagtaag agaattatgc agtgctgcca taaccatgag      780
tgataacact gcggccaact tacttctgac aacgatcgga ggaccgaagg agctaaccgc      840 tttttttgcac aacatggggg atcatgtaac tcgccttgat cgttgggaac cggagctgaa     900
tgaagccata ccaaacgacg agcgtgacac cacgatgcct gcagcaatgg caacaacgtt      960
gcgcaaacta ttaactggcg aactacttac tctagcttcc cggcaacaat taatagactg      1020
gatggaggcg gataaagttg caggaccact tctgcgctcg gcccttccgg ctggctggtt      1080
tattgctgat aaatctggag ccggtgagcg tgggtctcgc ggtatcattg cagcactggg      1140
gccagatggt aagccctccc gtatcgtagt tatctacacg acggggagtc aggcaactat      1200
ggatgaacga aatagacaga tcgctgagat aggtgcctca ctgattaagc attggtaact      1260
gtcagaccaa gtttactcat atatacttta gattgattta aaacttcatt tttaatttaa      1320
aaggatctag gtgaagatcc ttttttgataa tctcatgacc aaaatccctt aacgtgagtt      1380
ttcgttccac tgagcgtcag accccgtaga aaagatcaaa ggatcttctt gagatccttt      1440
ttttctgcgc gtaatctgct gcttgcaaac aaaaaaacca ccgctaccag cggtggtttg      1500
tttgccggat caagagctac caactctttt tccgaaggta actggcttca gcagagcgca      1560
gataccaaat actgtccttc tagtgtagcc gtagttagg                             1599
```

<210> SEQ ID NO 22
<211> LENGTH: 21
<212> TYPE: DNA
<213> ORGANISM: Artificial Sequence
<220> FEATURE:
<223> OTHER INFORMATION: HOP sequence

<400> SEQUENCE: 22

```
atgctttatt tcattaagtt g                                                21
```

<210> SEQ ID NO 23
<211> LENGTH: 103
<212> TYPE: DNA
<213> ORGANISM: Artificial Sequence
<220> FEATURE:
<223> OTHER INFORMATION: attL attachment site

<400> SEQUENCE: 23

```
gcattataaa aaagcattgc ttatcaattt gttgcaacga acaggtcact atcagtcaaa      60
atacaatcat tatttgattt caattttgtc ccactccctc ccg                        103
```

<210> SEQ ID NO 24
<211> LENGTH: 331
<212> TYPE: DNA
<213> ORGANISM: Artificial Sequence
<220> FEATURE:
<223> OTHER INFORMATION: PGK Promoter

<400> SEQUENCE: 24

```
aattctaccg ggtaggggag gcgcttttcc caaggcagtc tggagcatgc gctttagcag      60
ccccgctggg cacttggcgc tacacaagtg gcctctggcc tcgcacacat tccacatcca     120
ccggtaggcg ccaaccggct ccgttctttg gtggcccctt cgcgccacct tctactcctc     180
ccctagtcag gaagttcccc cccgccccgc agctcgcgtc gtgcaggacg tgacaaatgg     240
aagtagcacg tctcactagt ctcgtgcaga tggacagcac cgctgagcaa tggaagcggg     300
taggcctttg gggcagcggc caatagcagc t                                    331
```

<210> SEQ ID NO 25
<211> LENGTH: 25
<212> TYPE: DNA
<213> ORGANISM: Artificial Sequence
<220> FEATURE:
<223> OTHER INFORMATION: HOP' attH4X_F1 Primer

<400> SEQUENCE: 25

```
gagtgttttc caacttggtt ccatt                                            25
```

<210> SEQ ID NO 26
<211> LENGTH: 22
<212> TYPE: DNA
<213> ORGANISM: Artificial Sequence
<220> FEATURE:
<223> OTHER INFORMATION: PuroRev24 Primer

<400> SEQUENCE: 26

```
caccgtgggc ttgtactcgg tc                                               22
```

<210> SEQ ID NO 27
<211> LENGTH: 21
<212> TYPE: DNA
<213> ORGANISM: Artificial Sequence
<220> FEATURE:
<223> OTHER INFORMATION: pLIR-F1 Primer

<400> SEQUENCE: 27

```
ctgcatcgat tcagctagct g                                                21
```

<210> SEQ ID NO 28
<211> LENGTH: 22
<212> TYPE: DNA
<213> ORGANISM: Artificial Sequence
<220> FEATURE:
<223> OTHER INFORMATION: pLIR-R1 Primer

<400> SEQUENCE: 28

```
ctgatagtga cctgttcgtt gc                                               22
```

<210> SEQ ID NO 29
<211> LENGTH: 4906
<212> TYPE: DNA
<213> ORGANISM: Artificial Sequence
<220> FEATURE:
<223> OTHER INFORMATION: pPGKssPuro-attP4X (targeting vector)

<400> SEQUENCE: 29

```
gaattcctct gttacaggtc actaatacca tctaagtagt tgattcatag tgactgcata      60
tgttgtgttt tacagtatta tgtagtctgt tttttatgca aaatctaatt taatatattg     120
atatttatat catttacgt ttctcgttca gctttatttc attaagttgg cattataaaa     180
```

```
aagcattgct tatcaatttg ttgcaacgaa caggtcacta tcagtcaaaa taaaatcatt    240
atttgatttc aattttgtcc cactccctcc cgaattctac cgggtagggg aggcgctttt    300
cccaaggcag tctggagcat gcgctttagc agcccgctg gcacttggcg ctacacaagt    360
ggcctctggc ctcgcacaca ttccacatcc accggtagcg ccaaccggct ccgttctttg    420 gtggccccatt cgcgccactt ctactcctcc cctagtcagg aagtttcccc ccgccccgc    480 agctcgcgtc gtgcaggacg tgacaaatgg aagtagcacg tctcactagt ctcgtgcaga    540
tggacagcac cgctgagcaa tggaagcggg taggcctttg gggcagcggc caatagcagc    600
tttgctcctt cgcttctgg gctcagaggc tgggaagggg tgggtccggg ggcgggctca    660
ggggcgggct caggggcggg gcgggcgccc gaaggtcctc cggaggcccg gcattctgca    720
cgcttcaaaa gcgcacgtct gccgcgctgt tctcctcttc ctcatctccg gccttcga     780 ccaattcgct gtctgcgagg gccagctgtt ggggtgagta ctccctctca aaagcgggca    840
tgacttctgc gctaagattg tcagttccca aaaacgagga ggatttgata ttcacctggc    900
ccgcggtgat gcctttgagg gtggccgcgt ccatctggta gaaaagaca atctttttgt    960 tgtcaagctt gaggtgtggc aggcttgaga tctggccata cacttgagtg acaatgacat   1020
ccactttgcc tttctctcca caggtgtcca ctcccaggtc caactgcaga tgaccgagta   1080
caagcccacg gtgcgcctcg ccacccgcga cgacgtcccc cgggccgtac gcaccctcgc   1140
cgccgcgttc gccgactacc ccgccacgcg ccacaccgtc gacccggacc gccacatcga   1200
gcgggtcacc gagctgcaag aactcttcct cacgcgcgtc gggctcgaca tcggcaaggt   1260
gtgggtcgcg gacgacggcg ccgcggtggc ggtctggacc acgccggaga gcgtcgaagc   1320
gggggcggtg ttcgccgaga tcggcccgcg catggccgag ttgagcggtt cccggctggc   1380
cgcgcagcaa cagatggaag gcctcctggc gccgcaccgg cccaaggagc ccgcgtggtt   1440
cctggccacc gtcggcgtct cgcccgacca ccagggcaag ggtctgggca gcgccgtcgt   1500 gctcccgga gtggaggcgg ccgagcgcgc cggggtgccc gccttcctgg agacctccgc   1560
gccccgcaac ctccccttct acgagcggct cggcttcacc gtcaccgccg acgtcgaggt   1620
gcccgaagga ccgcgcacct ggtgcatgac ccgcaagccc ggtgcctgat ctagagctcg   1680
ctgatcagcc tcgactgtgc cttctagttg ccagccatct gttgtttgcc cctccccgt    1740 gccttccttg accctggaag tgccactccc actgtcctt tcctaataaa atgaggaaat   1800
tgcatcgcat tgtctgagta ggtgtcattc tattctgggg ggtgggtgg ggcaggacag    1860 caagggggag gattggaag acaatagcag gcatgctggg gatgcggtgg gctctatggc   1920
ttctgaggcg gaaagaacca gctggggctc gagatccact agttctagcc tcgaggctag   1980
agcggccgcc accgcggtgg agctccaatt cgccctatag tgagtcgtat tacgcgcgct   2040
cactggccgt cgttttacaa cgtcgtgact gggaaaaccc tggcgttacc caacttaatc   2100
gccttgcagc acatcccct ttcgccagct ggcgtaatag cgaagaggcc cgcaccgatc     2160
gcccttccca acagttgcgc agcctgaatg gcgaatggga cgcgccctgt agcggcgcat   2220
taagcgcggc gggtgtggtg gttacgcgca gcgtgaccgc tacacttgcc agcgccctag   2280
cgcccgctcc tttcgctttc ttcccttcct ttctcgccac gttcgccggc tttccccgtc   2340
aagctctaaa tcggggggctc cctttagggt tccgatttag tgctttacgg cacctcgacc   2400
ccaaaaaact tgattagggt gatggttcac gtagtgggcc atcgccctga tagacggttt   2460
ttcgcccttt gacgttggag tccacgttct ttaatagtgg actcttgttc caaactggaa   2520
caacactcaa ccctatctcg gtctattctt ttgatttata agggattttg ccgatttcgg   2580
```

```
cctattggtt aaaaaatgag ctgatttaac aaaaatttaa cgcgaatttt aacaaaatat   2640
taacgcttac aatttaggtg gcacttttcg gggaaatgtg cgcggaaccc ctatttgttt   2700
attttttctaa atacattcaa atatgtatcc gctcatgaga caataaccct gataaatgct  2760
tcaataatat tgaaaaagga agagtatgag tattcaacat ttccgtgtcg cccttattcc   2820
cttttttgcg gcattttgcc ttcctgtttt tgctcaccca gaaacgctgg tgaaagtaaa   2880
agatgctgaa gatcagttgg gtgcacgagt gggttacatc gaactggatc tcaacagcgg   2940
taagatcctt gagagttttc gccccgaaga acgttttcca atgatgagca cttttaaagt   3000
tctgctatgt ggcgcggtat tatcccgtat tgacgccggg caagagcaac tcggtcgccg   3060
catacactat tctcagaatg acttggttga gtactcacca gtcacagaaa agcatcttac   3120
ggatggcatg acagtaagag aattatgcag tgctgccata accatgagtg ataacactgc   3180
ggccaactta cttctgacaa cgatcggagg accgaaggag ctaaccgctt ttttgcacaa   3240
catgggggat catgtaactc gccttgatcg ttgggaaccg gagctgaatg aagccatacc   3300
aaacgacgag cgtgacacca cgatgcctgt agcaatggca acaacgttgc gcaaactatt   3360
aactggcgaa ctacttactc tagcttcccg gcaacaatta atagactgga tggaggcgga   3420
taaagttgca ggaccacttc tgcgctcggc ccttccggct ggctggttta ttgctgataa   3480
atctggagcc ggtgagcgtg ggtctcgcgg tatcattgca gcactggggc cagatggtaa   3540
gccctcccgt atcgtagtta tctacacgac ggggagtcag gcaactatgg atgaacgaaa   3600
tagacagatc gctgagatag gtgcctcact gattaagcat tggtaactgt cagaccaagt   3660
ttactcatat atactttaga ttgatttaaa acttcatttt taatttaaaa ggatctaggt   3720
gaagatcctt tttgataatc tcatgaccaa aatcccttaa cgtgagtttt cgttccactg   3780
agcgtcagac cccgtagaaa agatcaaagg atcttcttga gatcctttttt ttctgcgcgt  3840
aatctgctgc ttgcaaacaa aaaaaccacc gctaccagcg gtggtttgtt tgccggatca   3900
agagctacca actcttttttc cgaaggtaac tggcttcagc agagcgcaga taccaaatac   3960
tgtccttcta gtgtagccgt agttaggcca ccacttcaag aactctgtag caccgcctac   4020
atacctcgct ctgctaatcc tgttaccagt ggctgctgcc agtggcgata agtcgtgtct   4080
taccgggttg gactcaagac gatagttacc ggataaggcg cagcggtcgg gctgaacggg   4140
gggttcgtgc acacagccca gcttggagcg aacgacctac accgaactga gatacctaca   4200
gcgtgagcta tgagaaagcg ccacgcttcc cgaagggaga aaggcggaca ggtatccggt   4260
aagcggcagg gtcggaacag gagagcgcac gagggagctt ccagggggaa acgcctggta   4320
tctttatagt cctgtcgggt ttcgccacct ctgacttgag cgtcgatttt tgtgatgctc   4380
gtcaggggggg cggagcctat ggaaaaacgc cagcaacgcg gcctttttac ggttcctggc   4440
cttttgctgg ccttttgctc acatgttctt tcctgcgtta tcccctgatt ctgtggataa   4500
ccgtattacc gcctttgagt gagctgatac cgctcgccgc agccgaacga ccgagcgcag   4560
cgagtcagtg agcgaggaag cggaagagcg cccaatacgc aaaccgcctc tccccgcgcg   4620
ttggccgatt cattaatgca gctggcacga caggtttccc gactggaaag cgggcagtga   4680
gcgcaacgca attaatgtga gttagctcac tcattaggca ccccaggctt tacactttat   4740
gcttccggct cgtatgttgt gtggaattgt gagcggataa caatttcaca caggaaacag   4800
ctatgaccat gattacgcca agcgcgcaat taaccctcac taaagggaac aaaagctggg   4860
taccgggccc ccccctcgagg tcgacggtat cgataagctt gatatc                4906
```

<210> SEQ ID NO 30
<211> LENGTH: 5308
<212> TYPE: DNA
<213> ORGANISM: Artificial Sequence
<220> FEATURE:
<223> OTHER INFORMATION: pCMVssKZ-IntC3-CNLS (integrase expression plasmid)

<400> SEQUENCE: 30

| | | | | | |
|---|---|---|---|---|---|
| gaattcctca | catgttcttt | cctgcgttat | cccctgattc | tgtggataac | cgtattaccg | 60 |
| ccatgcatta | gttattaata | gtaatcaatt | acggggtcat | tagttcatag | cccatatatg | 120 |
| gagttccgcg | ttacataact | tacgtaaat | ggcccgcctg | gctgaccgcc | caacgacccc | 180 |
| cgcccattga | cgtcaataat | gacgtatgtt | cccatagtaa | cgccaatagg | gactttccat | 240 |
| tgacgtcaat | gggtggagta | tttacggtaa | actgcccact | tggcagtaca | tcaagtgtat | 300 |
| catatgccaa | gtacgcccc | tattgacgtc | aatgacggta | aatggcccgc | ctggcattat | 360 |
| gcccagtaca | tgaccttatg | ggactttcct | acttggcagt | acatctacgt | attagtcatc | 420 |
| gctattacca | tggtgatgcg | gttttggcag | tacatcaatg | ggcgtggata | gcggtttgac | 480 |
| tcacggggat | ttccaagtct | ccaccccatt | gacgtcaatg | ggagtttgtt | ttggcaccaa | 540 |
| aatcaacggg | actttccaaa | atgtcgtaac | aactccgccc | cattgacgca | aatgggcggt | 600 |
| aggcgtgtac | ggtgggaggt | ctatataagc | agagctggtt | tagtgaaccg | tcagatccgc | 660 |
| tagcaattcg | ctgtctgcga | gggccagctg | ttggggtgag | tactccctct | caaaagcggg | 720 |
| catgacttct | gcgctaagat | tgtcagtttc | caaaaacgag | gaggatttga | tattcacctg | 780 |
| gcccgcggtg | atgcctttga | gggtggccgc | gtccatctgg | tcagaaaaga | caatctttt | 840 |
| gttgtcaagc | ttgaggtgtg | gcaggcttga | gatctggcca | tacacttgag | tgacaatgac | 900 |
| atccactttg | cctttctctc | cacaggtgtc | cactcccagg | tccaactgca | gctcgaggtc | 960 |
| caccatggga | agaaggcgaa | gtcatgagcg | ccgggattta | ccccctaacc | tttatataag | 1020 |
| aaacaatgga | tattactgct | acagggaccc | aaggacgggt | aaagagtttg | gattaggcag | 1080 |
| agacaggcga | ttcgcaatca | ctgaagctat | acaggccaac | attgagttat | tttcaggaca | 1140 |
| caaacacaag | cctctgacag | cgagaatcaa | cagtgataat | tccgttacgt | tacattcatg | 1200 |
| gcttgatcgc | tacgaaaaaa | tcctggccag | cagaggaatc | aagcagaaga | cactcataaa | 1260 |
| ttacatgagc | aaaattaaag | caataaggag | gggtctgcct | gatgctccac | ttgaagacat | 1320 |
| caccacaaaa | gaaattgcgg | caatgctcaa | tggatacata | gacgagggca | aggcggcgtc | 1380 |
| agccaagtta | atcagatcaa | cgctgagcga | tgcattccga | gaggcaatag | ctgaaggcca | 1440 |
| tataacaaca | aaccatgtcg | ctgccactcg | cgcggcaaag | tcaaaggtaa | ggagatcaag | 1500 |
| acttacggct | gacgaatacc | tgaaaattta | tcaagcagca | gaatcatcac | catgttggct | 1560 |
| cagacttgca | atggaactgg | ctgttgttac | cgggcaacga | gttggtgact | tgtgcaaaat | 1620 |
| gaagtggtct | gatatcgtag | atggatatct | ttatgtcgag | caaagcaaaa | caggcgtaaa | 1680 |
| aattgccatc | ccaacagcat | tgcatattga | tgctctcgga | atatcaatga | aggaaacact | 1740 |
| tgataaatgc | aaagagattc | ttggcggaga | aaccataatt | gcatctactc | gtcgcgaacc | 1800 |
| gctctcatcc | ggcacagtat | caaggtattt | tatgcgcgca | cgaaaagcat | caggtctttc | 1860 |
| cttcgaaggg | gatccgccta | cctttcacga | gttgcgcagt | ttgtctgcaa | gactctatgg | 1920 |
| gaagcagata | agcgataagt | ttgctcaaca | tcttctcggg | cataagtcgg | tcaccatggc | 1980 |
| atcacagtat | cgtgatgaca | gaggcaggga | gtgggacaaa | attgaaatca | aatccggagg | 2040 |

```
cggccctaag aagaagagaa aggtatgata atctagagct cgctgatcag cctcgactgt    2100
gccttctagt tgccagccat ctgttgtttg cccctcccc  gtgccttcct tgaccctgga    2160
aggtgccact cccactgtcc tttcctaata aaatgaggaa attgcatcgc attgtctgag    2220
taggtgtcat tctattctgg ggggtgggt  ggggcaggac agcaaggggg aggattggga    2280
agacaatagc aggcatgctg gggatgcggt gggctctatg gcttctgagg cggaaagaac    2340
cagctggggc tcgagatcca ctagttctag cctcgaggct agagcggccg ccaccgcgt     2400 ggagctccaa ttcgccctat agtgagtcgt attacgcgcg ctcactggcc gtcgttttac    2460
aacgtcgtga ctgggaaaac cctggcgtta cccaacttaa tcgccttgca gcacatcccc    2520
ctttcgccag ctggcgtaat agcgaagagg cccgcaccga tcgcccttcc caacagttgc    2580
gcagcctgaa tggcgaatgg gacgcgccct gtagcggcgc attaagcgcg gcgggtgtgg    2640
tggttacgcg cagcgtgacc gctacacttg ccagcgccct agcgcccgct cctttcgctt    2700
tcttcccttc ctttctcgcc acgttcgccg gctttccccg tcaagctcta atcgggggc     2760 tccctttagg gttccgattt agtgcttac  ggcacctcga ccccaaaaaa cttgattagg    2820
gtgatggttc acgtagtggg ccatcgccct gatagacggt ttttcgccct ttgacgttgg    2880
agtccacgtt ctttaatagt ggactcttgt tccaaactgg aacaacactc aaccctatct    2940
cggtctattc ttttgattta aagggattt  tgccgatttc ggcctattgg ttaaaaaatg    3000
agctgattta acaaaaattt aacgcgaatt ttaacaaaat attaacgctt acaatttagg    3060
tggcactttt cggggaaatg tgcgcggaac ccctatttgt ttattttct  aaatacattc    3120 aaatatgtat ccgctcatga gacaataacc ctgataaatg cttcaataat attgaaaaag    3180
gaagagtatg agtattcaac atttccgtgt cgcccttatt ccctttttg  cggcattttg    3240 ccttcctgtt tttgctcacc cagaaacgct ggtgaaagta aaagatgctg aagatcagtt    3300
gggtgcacga gtgggttaca tcgaactgga tctcaacagc ggtaagatcc ttgagagttt    3360
tcgccccgaa gaacgttttc caatgatgag cacttttaaa gttctgctat gtggcgcggt    3420
attatcccgt attgacgccg ggcaagagca actcggtcgc cgcatacact attctcagaa    3480
tgacttggtt gagtactcac cagtcacaga aaagcatctt acggatggca tgacagtaag    3540
agaattatgc agtgctgcca taaccatgag tgataacact gcggccaact tacttctgac    3600
aacgatcgga ggaccgaagg agctaaccgc ttttttgcac aacatggggg atcatgtaac    3660
tcgccttgat cgttgggaac cggagctgaa tgaagccata ccaaacgacg agcgtgacac    3720
cacgatgcct gtagcaatgg caacaacgtt gcgcaaacta ttaactggcg aactacttac    3780
tctagcttcc cggcaacaat aatagactg  gatggaggcg gataaagttg caggaccact    3840
tctgcgctcg gcccttccgg ctggctggtt tattgctgat aaatctggag ccggtgagcg    3900
tgggtctcgc ggtatcattg cagcactggg gccagatggt aagccctccc gtatcgtagt    3960
tatctacacg acggggagtc aggcaactat ggatgaacga aatagacaga tcgctgagat    4020
aggtgcctca ctgattaagc attggtaact gtcagaccaa gtttactcat atatacttta    4080
gattgattta aaacttcatt tttaatttaa aaggatctag gtgaagatcc tttttgataa    4140
tctcatgacc aaaatccctt aacgtgagtt ttcgttccac tgagcgtcag accccgtaga    4200
aaagatcaaa ggatcttctt gagatccttt ttttctgcgc gtaatctgct gcttgcaaac    4260
aaaaaaacca ccgctaccag cggtggtttg tttgccggat caagagctac caactctttt    4320
tccgaaggta actggcttca gcagagcgca gataccaaat actgtccttc tagtgtagcc    4380
gtagttaggc caccacttca agaactctgt agcaccgcct acatacctcg ctctgctaat    4440
```

```
cctgttacca gtggctgctg ccagtggcga taagtcgtgt cttaccgggt tggactcaag    4500
acgatagtta ccgataagg cgcagcggtc gggctgaacg gggggttcgt gcacacagcc     4560
cagcttggag cgaacgacct acaccgaact gagataccta cagcgtgagc tatgagaaag    4620
cgccacgctt cccgaaggga aaaggcgga caggtatccg gtaagcggca gggtcggaac     4680
aggagagcgc acgagggagc ttccagggg aaacgcctgg tatctttata gtcctgtcgg     4740
gtttcgccac ctctgacttg agcgtcgatt tttgtgatgc tcgtcagggg ggcggagcct    4800
atggaaaaac gccagcaacg cggccttttt acggttcctg gccttttgct ggccttttgc    4860
tcacatgttc tttcctgcgt tatcccctga ttctgtggat aaccgtatta ccgcctttga    4920
gtgagctgat accgctcgcc gcagccgaac gaccgagcgc agcgagtcag tgagcgagga    4980
agcggaagag cgcccaatac gcaaaccgcc tctccccgcg cgttggccga ttcattaatg    5040
cagctggcac gacaggtttc ccgactggaa agcgggcagt gagcgcaacg caattaatgt    5100
gagttagctc actcattagg caccccaggc tttacacttt atgcttccgg ctcgtatgtt    5160
gtgtggaatt gtgagcggat aacaatttca cacaggaaac agctatgacc atgattacgc    5220
caagcgcgca attaaccctc actaaaggga caaaagctg gtaccgggc cccccctcga      5280 ggtcgacggt atcgataagc ttgatatc                                       5308
```

<210> SEQ ID NO 31
<211> LENGTH: 21
<212> TYPE: DNA
<213> ORGANISM: Artificial Sequence
<220> FEATURE:
<223> OTHER INFORMATION: attH4X attachment site

<400> SEQUENCE: 31

```
acgctttatt tcattaagtt g                                              21
```

<210> SEQ ID NO 32
<211> LENGTH: 1655
<212> TYPE: DNA
<213> ORGANISM: Artificial Sequence
<220> FEATURE:
<223> OTHER INFORMATION: Integrant E. coli colony generated using C3
      harbouring the lactamase cassette

<400> SEQUENCE: 32

```
tgaatccgtt gaagcctgct tttttatact aagttggcat tataaaaaag cattgcttat     60
caatttgttg caacgaacag gtcactatca gtcaaaataa aatcattatt tgatttcccg    120
gtgatgttca ggtggcactt tcggggaaa tgtgcgcgga accctatttt gtttattttt     180
ctaaatacat tcaaatatgt atccgctcat gagacaataa ccctgataaa tgcttcaata    240
atattgaaaa aggaagagta tgagtattca acatttccgt gtcgccctta ttccctttt     300 tgcggcattt tgccttcctg tttttgctca cccagaaacg ctggtgaaag taaaagatgc    360
tgaagatcag ttgggtgcac gagtgggtta catcgaactg gatctcaaca gcggtaagat    420
ccttgagagt tttcgccccg aagaacgttt tccaatgatg agcacttta aagttctgct    480 atgtggcgcg gtattatccc gtattgacgc cgggcaagag caactcggtc gccgcataca    540
ctattctcag aatgacttgg ttgagtactc accagtcaca gaaaagcatc ttacggatgg    600
catgacagta agagaattat gcagtgctgc cataaccatg agtgataaca ctgcggccaa    660
cttacttctg acaacgatcg gaggaccgaa ggagctaacc gcttttttgc acaacatggg    720
ggatcatgta actcgccttg atcgttggga accggagctg aatgaagcca taccaaacga    780
```

```
cgagcgtgac accacgatgc ctgcagcaat ggcaacaacg ttgcgcaaac tattaactgg    840
cgaactactt actctagctt cccggcaaca attaatagac tggatggagg cggataaagt    900
tgcaggacca cttctgcgct cggcccttcc ggctggctgg tttattgctg ataaatctgg    960
agccggtgag cgtgggtctc gcggtatcat tgcagcactg gggccagatg gtaagccctc   1020
ccgtatcgta gttatctaca cgacggggag tcaggcaact atggatgaac gaaatagaca   1080
gatcgctgag ataggtgcct cactgattaa gcattggtaa ctgtcagacc aagtttactc   1140
atatatactt tagattgatt taaaacttca ttttaatttt aaaaggatct aggtgaagat   1200
cctttttgat aatctcatga ccaaaatccc ttaacgtgag ttttcgttcc actgagcgtc   1260 agacccegta gaaaagatca aaggatcttc ttgagatcct ttttttctgc gcgtaatctg   1320
ctgcttgcaa acaaaaaaac caccgctacc agcggtggtt tgtttgccgg atcaagagct   1380
accaactctt ttccgaaggt aactggcttc agcagagcgc agataccaaa tactgtcctt   1440
ctagtgtagg aattccacag aattccgtct gttacaggtc actaatacca tctaagtagt   1500
tgattcatag tgactgcata tattgtgttt tacagtatta tgtagtctgt tttttatgca   1560
aaatctaatt taatatattg atatttatat catttttacgt ttctcgttca gctttttat    1620 actaacttga gcgaaacggg aaggtaaaaa gacat                              1655

<210> SEQ ID NO 33
<211> LENGTH: 558
<212> TYPE: DNA
<213> ORGANISM: Artificial Sequence
<220> FEATURE:
<223> OTHER INFORMATION: attL recombinant HT1080 clone 3

<400> SEQUENCE: 33
ctttatgacc cagtcatcgt tggtttggtc ttttcacata gtcccatgtt tcttggagat     60
tttgttcatt ccttctcatt cttttttctc taatcttgtc ctcatgcttt atttcattaa    120
gttggcatta taaaaaagca ttgcttatca atttgttgca acgaacaggt cactatcagt    180
caaaatacaa tcattatttg atttcaattt tgtcccactc cctcccgaat tctaccgggt    240
aggggaggcg cttttcccaa ggcagtctgg agcatgcgct ttagcagccc cgctgggcac    300
ttggcgctac acaagtggcc tctggcctcg cacacattcc acatccaccg gtaggcgcca    360
accggctccg ttctttggtg gccccttcgc gccaccttct actcctcccc tagtcaggaa    420
gttccccccc gccccgcagc tcgcgtcgtg caggacgtga caaatggaag tagcacgtct    480
cactagtctc gtgcagatgg acagcaccgc tgagcaatgg aagcgggtag gcctttgggg    540
cagcggccaa tagcagct                                                  558

<210> SEQ ID NO 34
<211> LENGTH: 558
<212> TYPE: DNA
<213> ORGANISM: Artificial Sequence
<220> FEATURE:
<223> OTHER INFORMATION: attL recombinant HT1080 clone 19

<400> SEQUENCE: 34
gattcggtaa ccaatcaaat gtaagcttgg tcttttcaca taatcccata ttttttggag     60
gctttgttca tttctttttca ttcttttttc tctaatctgt cttcatgctt tatttcatta    120
agttggcatt ataaaaaagc attgcttatc aatttgttgc aacgaacagg tcactatcag    180
tcaaaataca atcattattt gatttcaatt ttgtcccact ccctcccgaa ttctaccggg    240
```

```
tagggggaggc gcttttccca aggcagtctg gagcatgcgc tttagcagcc ccgctgggca    300
cttggcgcta cacaagtggc ctctggcctc gcacacattc cacatccacc ggtaggcgcc    360
aaccggctcc gttctttggt ggccccttcg cgccaccttc tactcctccc ctagtcagga    420
agttcccccc cgcccgcag ctcgcgtcgt gcaggacgtg acaaatggaa gtagcacgtc     480
tcactagtct cgtgcagatg gacagcaccg ctgagcaatg gaagcgggta ggcctttggg    540
gcagcggcca atagcagc                                                  558
```